US010307047B2

(12) United States Patent
Scheller et al.

(10) Patent No.: US 10,307,047 B2
(45) Date of Patent: Jun. 4, 2019

(54) ILLUMINATED MIRCORSURGICAL PROBE

(71) Applicant: Kogent Surgical, LLC, Chesterfield, MO (US)

(72) Inventors: Gregg D Scheller, Wildwood, MO (US); Michael J O'Laughlin, St. Charles, MO (US)

(*) Notice: Subject to any disclaimer, the term of this patent is extended or adjusted under 35 U.S.C. 154(b) by 598 days.

(21) Appl. No.: 15/181,494

(22) Filed: Jun. 14, 2016

(65) Prior Publication Data

US 2017/0007107 A1 Jan. 12, 2017

Related U.S. Application Data

(60) Provisional application No. 62/189,508, filed on Jul. 7, 2015.

(51) Int. Cl.
| | |
|---|---|
| *A61B 90/30* | (2016.01) |
| *A61B 1/07* | (2006.01) |
| *A61M 1/00* | (2006.01) |
| *G02B 6/36* | (2006.01) |
| *G02B 6/44* | (2006.01) |

(52) U.S. Cl.
CPC .............. *A61B 1/07* (2013.01); *A61B 90/30* (2016.02); *A61M 1/0092* (2014.02); *G02B 6/3624* (2013.01); *G02B 6/4471* (2013.01); *A61B 2090/306* (2016.02); *A61B 2217/005* (2013.01); *A61B 2218/007* (2013.01)

(58) Field of Classification Search
CPC . A61B 1/06; A61B 1/07; A61B 90/30; A61M 1/0092; G02B 6/3624
USPC ....................................................... 606/249
See application file for complete search history.

(56) References Cited

U.S. PATENT DOCUMENTS

| | | | |
|---|---|---|---|
| 5,010,300 A | 5/1991 | Williams | |
| 5,013,300 A | 5/1991 | Williams | |
| 5,213,092 A * | 5/1993 | Uram | A61B 1/00165 600/156 |
| 5,588,952 A * | 12/1996 | Dandolu | A61M 1/008 362/572 |
| 5,651,783 A | 7/1997 | Reynard | |
| 8,870,761 B2 | 8/2014 | Vayser et al. | |
| 9,072,452 B2 | 7/2015 | Vayser et al. | |
| 2002/0009275 A1 | 1/2002 | Williams et al. | |
| 2005/0171408 A1* | 8/2005 | Parker | A61B 90/35 600/249 |
| 2013/0012783 A1* | 1/2013 | Vayser | A61B 1/00135 600/249 |

(Continued)

OTHER PUBLICATIONS

Eigr Saber Waveguide Brochure (Rev B) 2013.

*Primary Examiner* — Si Ming Ku

(57) ABSTRACT

An illuminated microsurgical probe may include a handle, a diffuser, an aspiration conduit, and an optic fiber bundle. The diffuser may include a diffuser distal end, a diffuser proximal end, and a diffuser inner bore. The handle may include a handle distal end, a handle proximal end, and a handle inner bore. The aspiration conduit may include an aspiration conduit distal end and an aspiration conduit proximal end. The aspiration conduit distal end may be disposed in the diffuser inner bore and the aspiration conduit proximal end may be disposed in the handle inner bore. The optic fiber bundle may include an optic fiber bundle distal end and an optic fiber bundle proximal end. The optic fiber bundle distal end may be disposed in the diffuser inner bore.

20 Claims, 13 Drawing Sheets

(56) References Cited

U.S. PATENT DOCUMENTS

2015/0148770 A1    5/2015   Arnone et al.
2015/0374429 A1   12/2015   Scheller et al.

\* cited by examiner

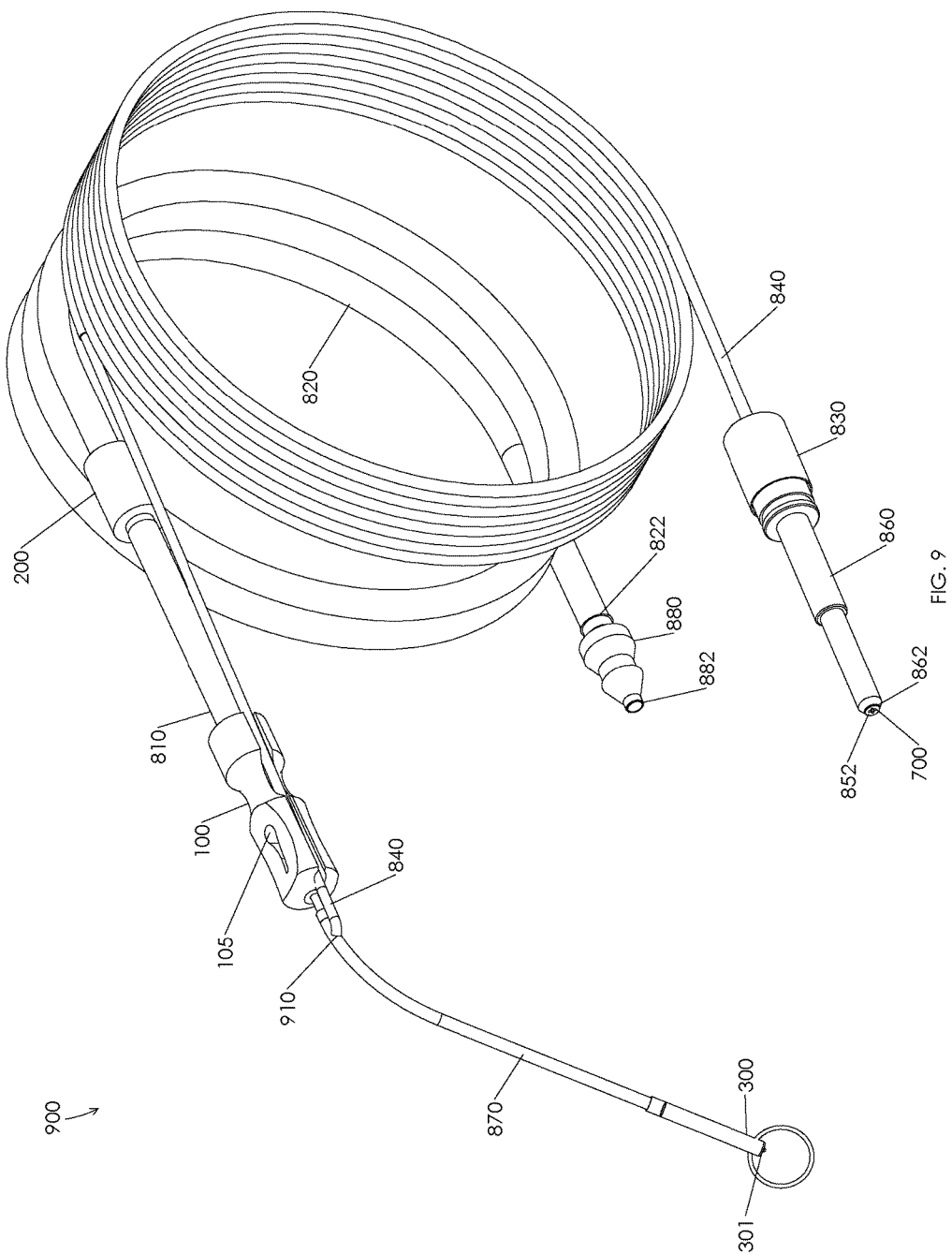

ILLUMINATED MIRCORSURGICAL PROBE

CROSS-REFERENCE TO RELATED APPLICATIONS

This Application claims the benefit of U.S. Provisional Application No. 62/189,508, filed Jul. 7, 2015.

FIELD OF THE INVENTION

The present disclosure relates to a microsurgical probe, and, more particularly, to an illuminated microsurgical probe.

BACKGROUND OF THE INVENTION

A variety of surgical procedures require removal of debris from a surgical site, e.g., blood, irrigation fluid, tissue, bone, etc., may require removal from a surgical site during a surgical procedure. Many microsurgical procedures require illumination of a surgical site to allow a surgeon to adequately visualize the surgical site during a surgical procedure. Some microsurgical procedures may require removal of debris from a surgical site and illumination of the surgical site. For example, a neurosurgical procedure for a cavernous malformation and a spinal surgical procedure for a laminectomy may require both removal of debris from a surgical site and illumination of the surgical site. Accordingly, there is a need for a microsurgical probe having both aspiration and illumination functionality.

BRIEF SUMMARY OF THE INVENTION

In one or more embodiments, an illuminated microsurgical probe may comprise a handle, a diffuser, an aspiration conduit, and an optic fiber bundle. Illustratively, the diffuser may comprise a diffuser distal end, a diffuser proximal end, and a diffuser inner bore. In one or more embodiments, the handle may comprise a handle distal end, a handle proximal end, and a handle inner bore. Illustratively, the aspiration conduit may comprise an aspiration conduit distal end and an aspiration conduit proximal end. In one or more embodiments, the aspiration conduit distal end may be disposed in the diffuser inner bore and the aspiration conduit proximal end may be disposed in the handle inner bore. Illustratively, the optic fiber bundle may comprise an optic fiber bundle distal end and an optic fiber bundle proximal end. In one or more embodiments, the optic fiber bundle distal end may be disposed in the diffuser inner bore.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIG. 9 is a schematic diagram illustrating an assembled illuminated microsurgical probe.

DETAILED DESCRIPTION OF AN ILLUSTRATIVE EMBODIMENT

Figure 1A:
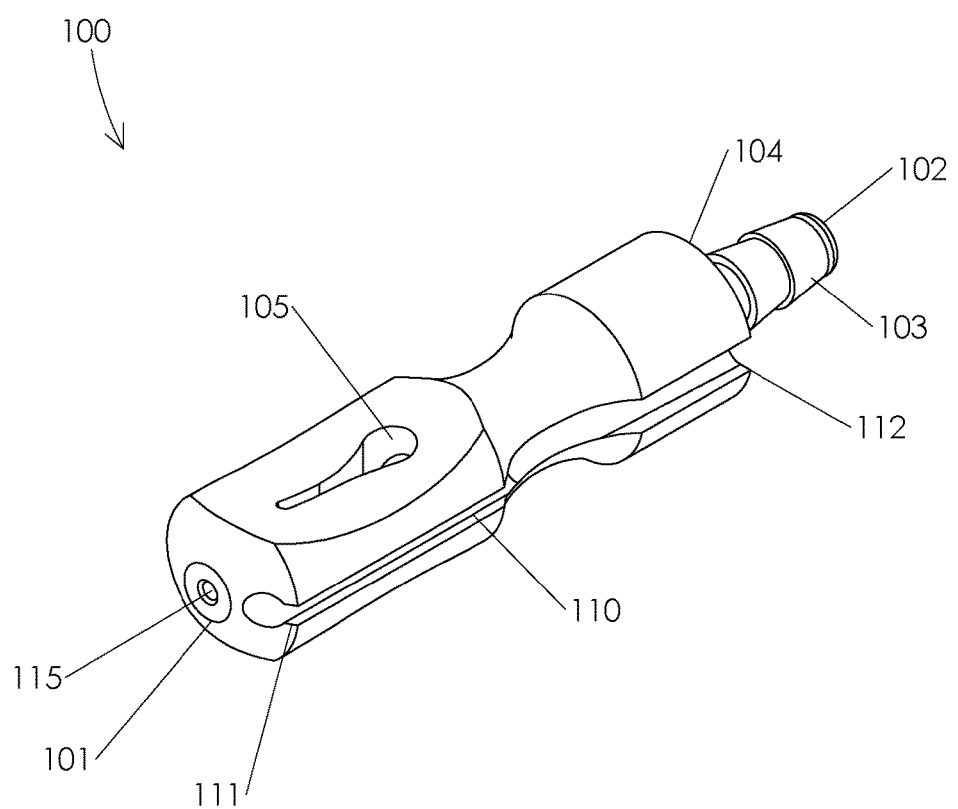
FIGS. 1A, 1B, 1C, 1D, 1E, and 1F are schematic diagrams illustrating a handle.
Figure 1B:
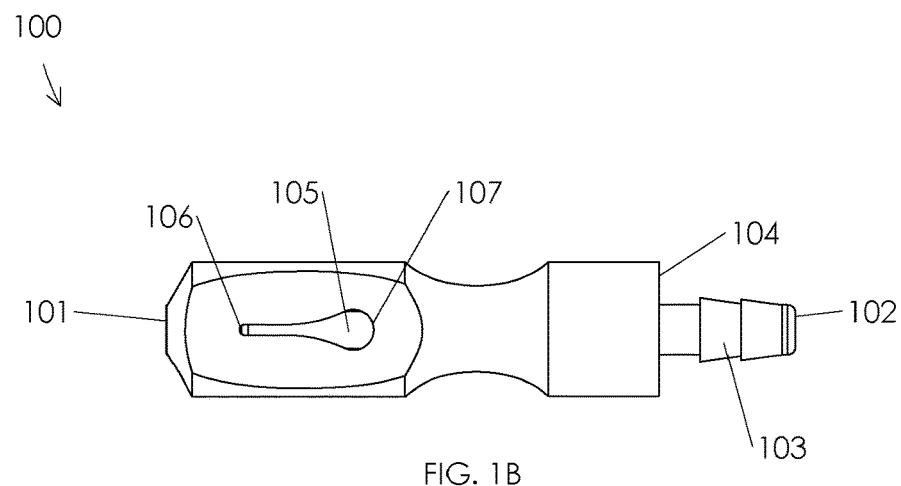
Figure 1C:
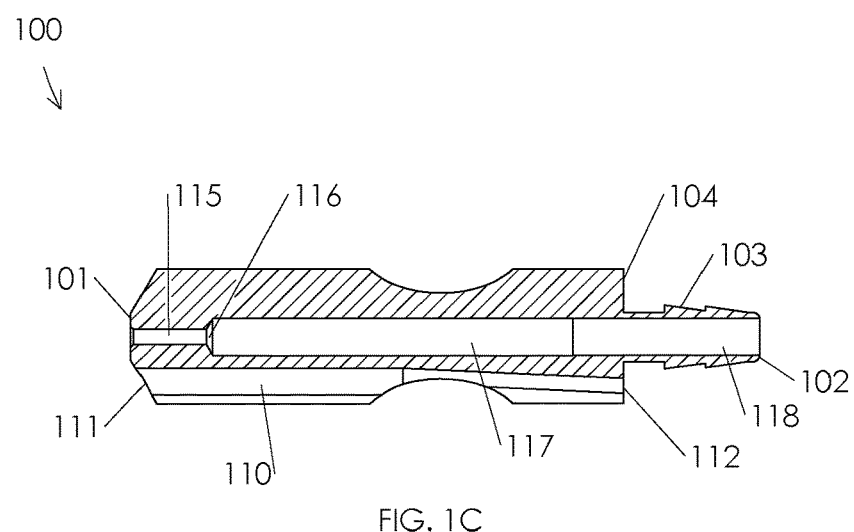
Figure 1D:
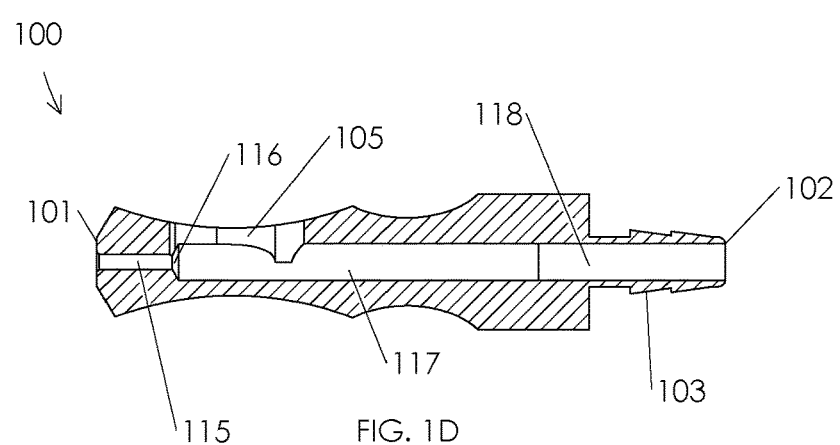
Figure 1E:
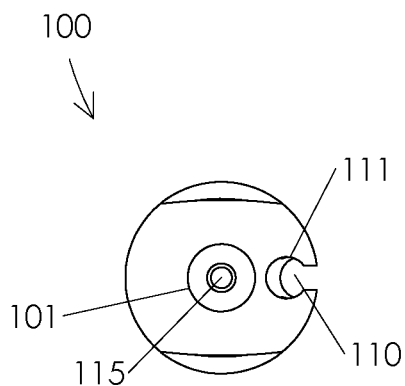
Figure 1F:
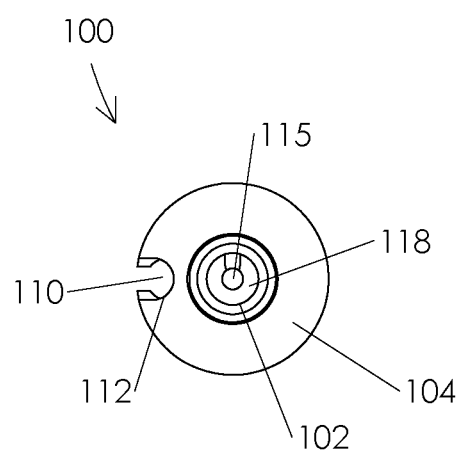

FIGS. 1A, 1B, 1C, 1D, 1E, and 1F are schematic diagrams illustrating a handle 100. FIG. 1A illustrates an isometric view of handle 100. Illustratively, handle 100 may comprise a handle distal end 101, a handle proximal end 102, a barb 103, a distal sleeve interface 104, a vent 105, an optic fiber bundle jacketing housing 110, and a handle distal chamber 115. In one or more embodiments, optic fiber bundle jacketing housing 110 may comprise an optic fiber bundle jacketing housing distal end 111 and an optic fiber jacketing housing proximal end 112. Illustratively, optic fiber bundle jacketing housing distal end 111 may be adjacent to handle distal end 101. In one or more embodiments, optic fiber bundle jacketing housing proximal end 112 may be adjacent to distal sleeve interface 104. FIG. 1B illustrates a top view of handle 100. Illustratively, vent 105 may comprise a vent distal end 106 and a vent proximal end 107. In one or more embodiments, vent 105 may have a variable width, e.g., vent 105 may have a first width at vent distal end 106 and vent 105 may have a second width at vent proximal end 107. Illustratively, the second width may be greater than the first width. In one or more embodiments, the first width may be greater than the second width. FIG. 1C illustrates a cross-sectional view in a transverse plane of handle 100. FIG. 1D illustrates a cross-sectional view in a sagittal plane of handle 100. In one or more embodiments, handle 100 may comprise a handle distal chamber 115, a handle focused taper 116, a handle inner bore 117, and a handle proximal chamber 118. FIG. 1E illustrates a front view of handle 100. FIG. 1F illustrates a back view of handle 100. In one or more embodiments, handle 100 may be may be manufactured from any suitable material, e.g., polymers, metals, metal alloys, etc., or from any combination of suitable materials.

Figure 2A:
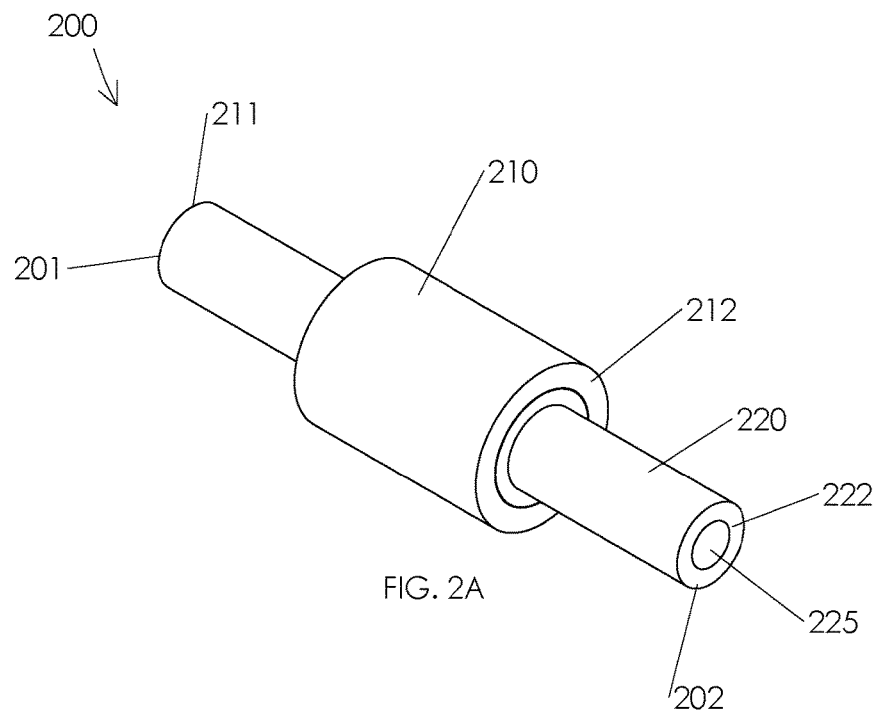
FIGS. 2A and 2B are schematic diagrams illustrating a swivel.
Figure 2B:
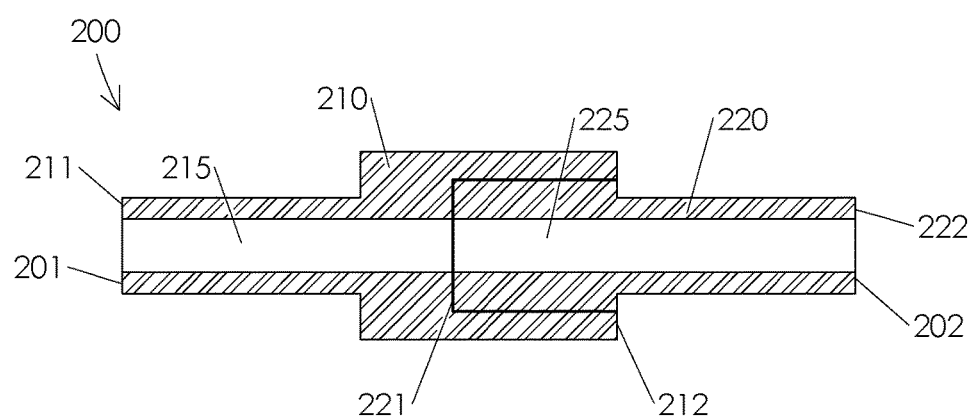

FIGS. 2A and 2B are schematic diagrams illustrating a swivel 200. FIG. 2A illustrates an isometric view of swivel 200. In one or more embodiments, swivel 200 may comprise a swivel distal end 201, swivel proximal end 202, an outer swivel component 210, and an inner swivel component 220. FIG. 2B illustrates a cross-sectional view in a sagittal plane of swivel 200. Illustratively, outer swivel component 210 may comprise an outer swivel component distal end 211, an outer swivel component proximal end 212, and an outer swivel component inner bore 215. In one or more embodiments, inner swivel component 220 may comprise an inner swivel component distal end 221, an inner swivel component proximal end 222, and an inner swivel component inner bore 225. Illustratively, a portion of inner swivel component 220 may be disposed within a portion of outer swivel component 210, e.g., inner swivel component distal end 221 may be disposed within a portion of outer swivel component 210. In one or more embodiments, a portion of inner swivel component 220 may be disposed within a portion of outer swivel component 210 wherein inner swivel component proximal end 222 is swivel proximal end 202 and outer swivel component distal end 211 is swivel distal end 201.

Illustratively, a portion of inner swivel component 220 may be disposed within a portion of outer swivel component 210 wherein inner swivel component distal end 221 is disposed between outer swivel component distal end 211 and outer swivel component proximal end 212. In one or more embodiments, a portion of inner swivel component 220 may be disposed within a portion of outer swivel component 210 wherein outer swivel component proximal end 212 is disposed between inner swivel component distal end 221 and inner swivel component proximal end 222. Illustratively, a portion of inner swivel component 220 may be fixed within a portion of outer swivel component 210 wherein inner swivel component 220 is configured to rotate relative to outer swivel component 210. In one or more embodiments, a portion of inner swivel component 220 may be fixed within a portion of outer swivel component 210 wherein outer swivel component 210 is configured to rotate relative to inner swivel component 220. Illustratively, a portion of inner swivel component 220 may be disposed in a portion of outer swivel component 210 wherein inner swivel component inner bore 225 is aligned with outer swivel component inner bore 215, e.g., a portion of inner swivel component 220 may be disco posed in a portion of outer swivel component 210 wherein inner swivel component inner bore 225 and outer swivel component inner bore 215 comprise a single inner bore of swivel 200. In one or more embodiments, swivel 200 may be may be manufactured from any suitable material, e.g., polymers, metals, metal alloys, etc., or from any combination of suitable materials.

Figure 3A:
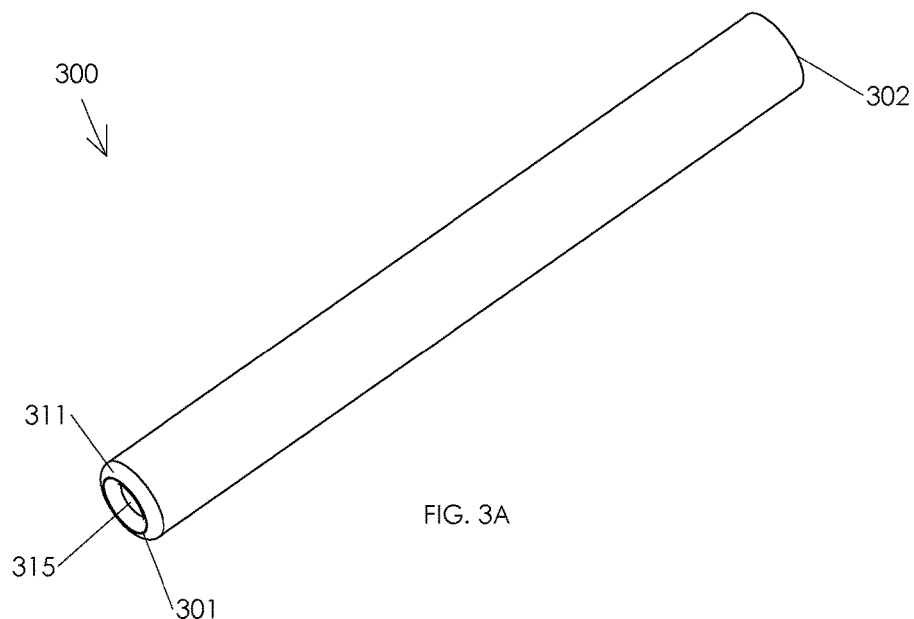
FIGS. 3A, 3B, 3C, 3D, 3E, and 3F are schematic diagrams illustrating a diffuser.
Figure 3B:
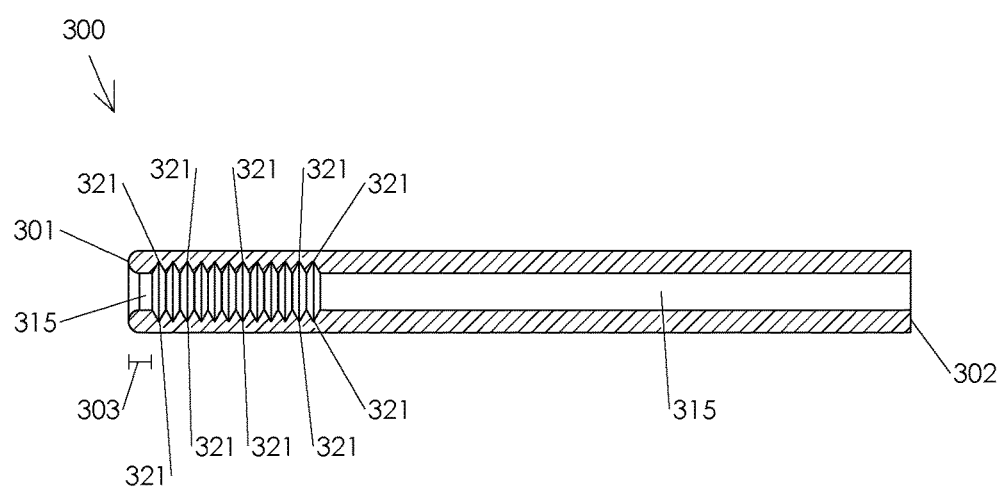

FIGS. 3A, 3B, 3C, 3D, 3E, and 3F are schematic diagrams illustrating a diffuser 300. FIG. 3A illustrates an isometric view of diffuser 300. In one or more embodiments, diffuser 300 may comprise a diffuser distal end 301, a diffuser proximal end 302, a first distal taper 311 and a diffuser inner bore 315. FIG. 3B illustrates a cross-sectional view in a sagittal plane of diffuser 300. Illustratively, diffuser 300 may comprise a first atraumatic offset 303 and a first diffusion notch 321. In one or more embodiments, first atraumatic offset 303 may be configured to reduce a risk of unintentional trauma during a surgical procedure. For example, first distal taper 311 may be configured to reduce a surface area of diffuser distal end 301 which may increase a risk of unintentional trauma during a surgical procedure, e.g., reducing a surface area of diffuser distal end 301 may increase a risk of cutting a tissue during an aspiration of a surgical site. In one or more embodiments, first atraumatic offset 303 may be configured to decrease a risk of cutting a tissue during an aspiration of a surgical site, e.g., first atraumatic offset 303 may be configured to decrease a risk of cutting a tissue during an aspiration of a surgical site by increasing a surface area of diffuser distal end 301. Illustratively, first atraumatic offset 303 may have a length in a range of 0.02 to 0.04 inches, e.g., first atraumatic offset 303 may have a length of 0.03 inches. In one or more embodiments, first atraumatic offset 303 may have a length of less than 0.02 inches or greater than 0.04 inches.

Illustratively, diffuser 300 may be configured to diffuse light, e.g., diffuser 300 may be configured to diffuse light to illuminate a surgical site. In one or more embodiments, diffuser 300 may be configured to diffuse light by diffuse reflection. Illustratively, diffuser 300 may be may be manufactured from any suitable material, e.g., polymers, metals, metal alloys, etc., or from any combination of suitable materials. In one or more embodiments, diffuser 300 may be manufactured from a material configured to increase an efficiency of diffuse reflection. Illustratively, diffuser 300 may be manufactured from an optically transparent material, e.g., diffuser 300 may be manufactured from polycarbonate, acrylic, etc. In one or more embodiments, diffuser 300 may be manufactured from a material having an index of refraction that is similar to an index of refraction of optic fiber bundle 850, e.g., diffuser 300 may be manufactured from a material having an index of refraction that is not more than 10.0 to 30.0 percent less than an index of refraction of optic fiber bundle 850. Illustratively, diffuser 300 may be manufactured from a material having an index of refraction that is not more than 10.0 to 30.0 percent greater than an index of refraction of optic fiber bundle 850. In one or more embodiments, diffuser 300 may be manufactured from a material having an index of refraction that is not more than 10.0 percent less than an index of refraction of optic fiber bundle 850, e.g., diffuser 300 may be manufactured from a material having an index of refraction that is not more than 10.0 percent greater than an index of refraction of optic fiber bundle 850. Illustratively, first diffusion notch 321 may be configured to diffuse light, e.g., first diffusion notch 321 may be configured to diffuse light by diffuse reflection. In one or more embodiments, diffuser 300 may comprise a plurality of first diffusion notches 321, e.g., diffuser 300 may comprise a plurality of first diffusion notches 321 wherein each first diffusion notch 321 of the plurality of first diffusion notches 321 is configured to diffuse light. For example, a first particular first diffusion notch 321 of the plurality of first diffusion notches 321 may be configured to diffuse an incident ray of light at a first plurality of angles creating a plurality of first non-incident rays of light and a second particular first diffusion notch 321 of the plurality of first diffusion notches 321 may be configured to diffuse a first non-incident ray of light of the plurality of first non-incident rays of light at a second plurality of angles creating a plurality of second non-incident rays of light.

Figure 3C:
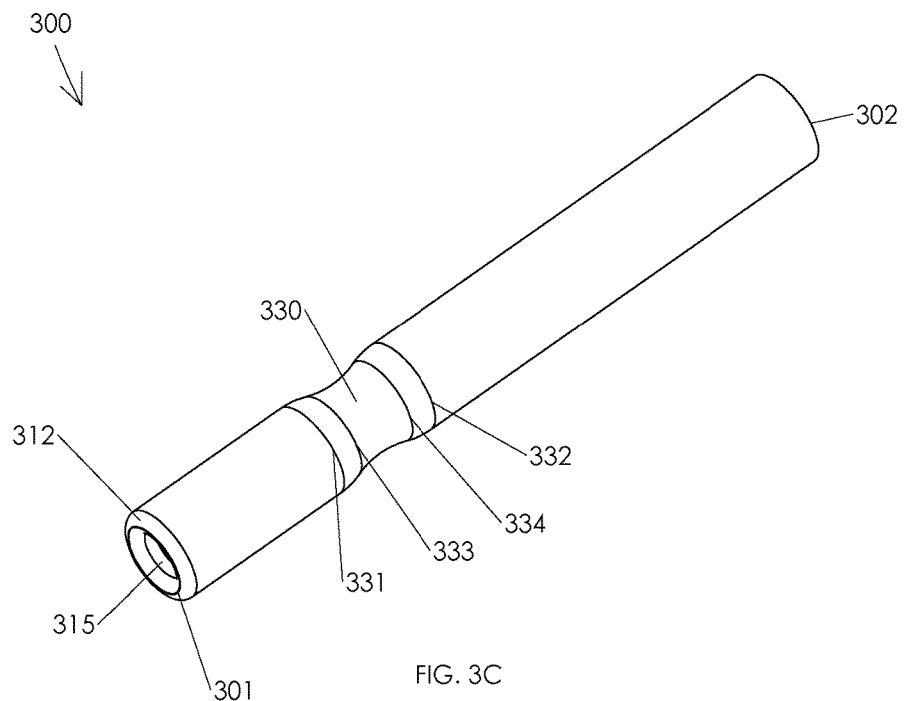
Figure 3D:
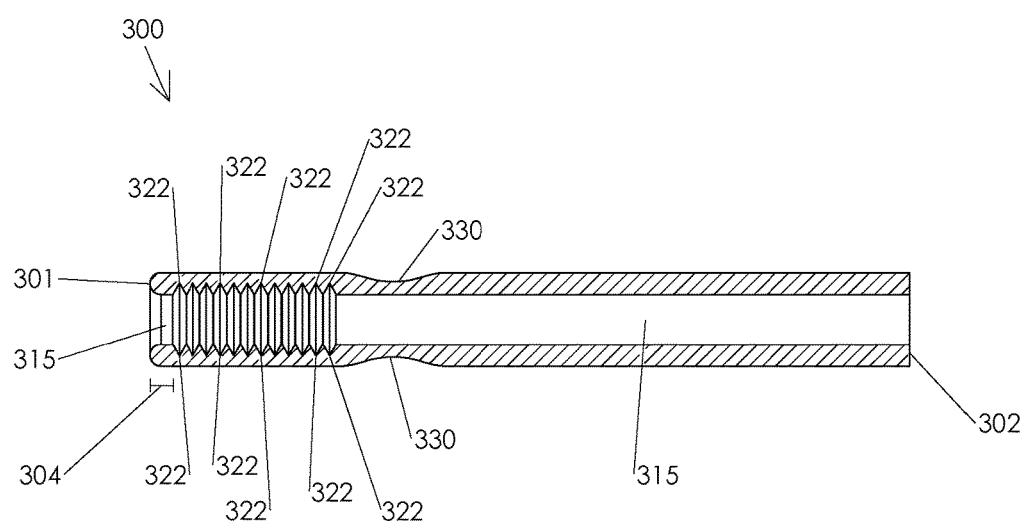

FIG. 3C illustrates an isometric view of diffuser 300. In one or more embodiments, diffuser 300 may comprise a diffuser distal end 301, a diffuser proximal end 302, a second distal taper 312, a diffuser inner bore 315, and a diffusion indentation 330. Illustratively, diffusion indentation 330 may comprise a diffusion indentation distal end 331, a diffusion indentation proximal end 332, a diffusion indentation distal gradient increase 333, and a diffusion indentation proximal gradient increase 334. FIG. 3D illustrates a cross-sectional view in a sagittal plane of diffuser 300. Illustratively, diffuser 300 may comprise a second atraumatic offset 304 and a second diffusion notch 322. In one or more embodiments, second atraumatic offset 304 may be configured to reduce a risk of unintentional trauma during a surgical procedure. For example, second distal taper 312 may be configured to reduce a surface area of diffuser distal end 301 which may increase a risk of unintentional trauma during a surgical procedure, e.g., reducing a surface area of diffuser distal end 301 may increase a risk of cutting a tissue during an aspiration of a surgical site. In one or more embodiments, second atraumatic offset 304 may be configured to decrease a risk of cutting a tissue during an aspiration of a surgical site, e.g., second atraumatic offset 304 may be configured to decrease a risk of cutting a tissue during an aspiration of a surgical site by increasing a surface area of diffuser distal end 301. Illustratively, second atraumatic offset 304 may have a length in a range of 0.02 to 0.04 inches, e.g., second atraumatic offset 304 may have a length of 0.03 inches. In one or more embodiments, second atraumatic offset 304 may have a length of less than 0.02 inches or greater than 0.04 inches.

Illustratively, diffuser 300 may be configured to diffuse light, e.g., diffuser 300 may be configured to diffuse light to illuminate a surgical site. In one or more embodiments, diffuser 300 may be configured to diffuse light by diffuse reflection. Illustratively, diffuser 300 may be may be manufactured from any suitable material, e.g., polymers, metals, metal alloys, etc., or from any combination of suitable materials. In one or more embodiments, diffuser 300 may be manufactured from a material configured to increase an efficiency of diffuse reflection. Illustratively, diffuser 300 may be manufactured from an optically transparent material, e.g., diffuser 300 may be manufactured from polycarbonate, acrylic, etc. In one or more embodiments, diffuser 300 may be manufactured from a material having an index of refraction that is similar to an index of refraction of optic fiber bundle 850, e.g., diffuser 300 may be manufactured from a material having an index of refraction that is not more than 10.0 to 30.0 percent less than an index of refraction of optic fiber bundle 850. Illustratively, diffuser 300 may be manufactured from a material having an index of refraction that is not more than 10.0 to 30.0 percent greater than an index of refraction of optic fiber bundle 850. In one or more embodiments, diffuser 300 may be manufactured from a material having an index of refraction that is not more than 10.0 percent less than an index of refraction of optic fiber bundle 850, e.g., diffuser 300 may be manufactured from a material having an index of refraction that is not more than 10.0 percent greater than an index of refraction of optic fiber bundle 850. Illustratively, second diffusion notch 322 may be configured to diffuse light, e.g., second diffusion notch 322 may be configured to diffuse light by diffuse reflection. In one or more embodiments, diffuser 300 may comprise a plurality of second diffusion notches 322, e.g., diffuser 300 may comprise a plurality of second diffusion notches 322 wherein each second diffusion notch 322 of the plurality of second diffusion notches 322 is configured to diffuse light. For example, a first particular second diffusion notch 322 of the plurality of second diffusion notches 322 may be configured to diffuse an incident ray of light at a first plurality of angles creating a plurality of first non-incident rays of light and a second particular second diffusion notch 322 of the plurality of second diffusion notches 322 may be configured to diffuse a first non-incident ray of light of the plurality of first non-incident rays of light at a second plurality of angles creating a plurality of second non-incident rays of light.

Illustratively, diffusion indentation 330 may be configured to diffuse light, e.g., diffusion indentation 330 may be configured to diffuse light by diffuse reflection. For example, diffusion indentation 330 may be configured to diffuse an incident ray of light at a first plurality of angles creating a plurality of first non-incident rays of light and second diffusion notch 322 may be configured to diffuse a first non-incident ray of light of the plurality of first non-incident rays of light at a second plurality of angles creating a plurality of second non-incident rays of light. In one or more embodiments, diffusion indentation distal gradient increase 333 may be configured to diffuse light, e.g., diffusion indentation distal gradient increase 333 may be configured to diffuse light by diffuse reflection. For example, diffusion indentation distal gradient increase 333 may be configured to diffuse an incident ray of light at a first plurality of angles creating a plurality of first non-incident rays of light and second diffusion notch 322 may be configured to diffuse a first non-incident ray of light of the plurality of first non-incident rays of light at a second plurality of angles creating a plurality of second non-incident rays of light. Illustratively, diffusion indentation proximal gradient increase 334 may be configured to diffuse light, e.g., diffusion indentation proximal gradient increase 334 may be configured to diffuse light by diffuse reflection. For example, diffusion indentation proximal gradient increase 334 may be configured to diffuse an incident ray of light at a first plurality of angles creating a plurality of first non-incident rays of light and second diffusion notch 322 may be configured to diffuse a first non-incident ray of light of the plurality of first non-incident rays of light at a second plurality of angles creating a plurality of second non-incident rays of light.

Figure 3E:
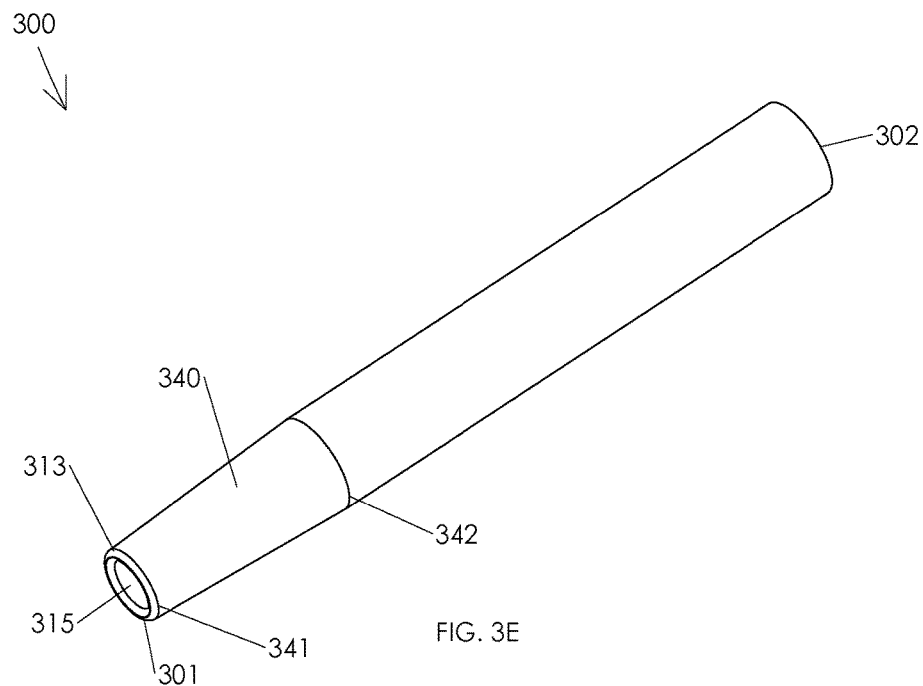
Figure 3F:
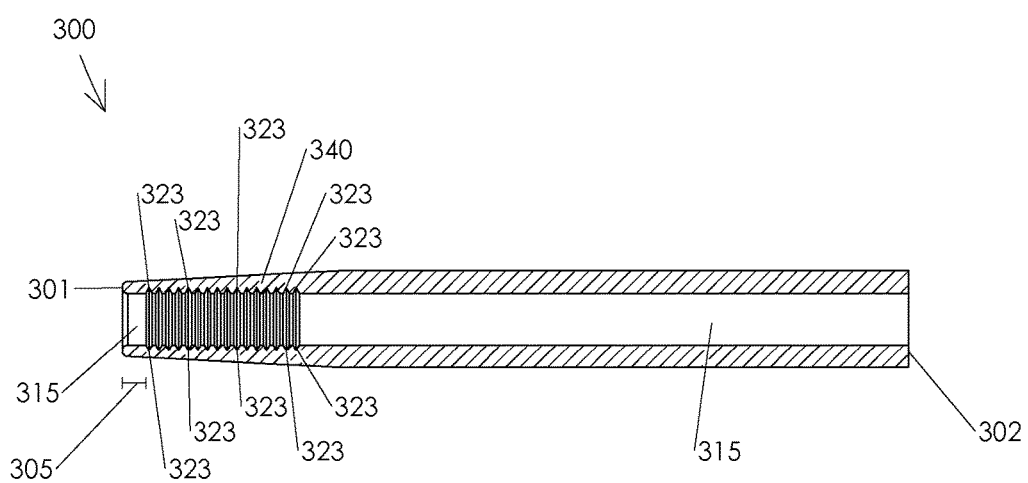

FIG. 3E illustrates an isometric view of diffuser 300. In one or more embodiments, diffuser 300 may comprise a diffuser distal end 301, a diffuser proximal end 302, a third distal taper 313, a diffuser inner bore 315, and a diffusion taper 340. Illustratively, diffusion taper 340 may comprise a diffusion taper distal end 341 and a diffusion taper proximal end 342. FIG. 3F illustrates a cross-sectional view in a sagittal plane of diffuser 300. Illustratively, diffuser 300 may comprise a third atraumatic offset 305 and a third diffusion notch 323. In one or more embodiments, third atraumatic offset 305 may be configured to reduce a risk of unintentional trauma during a surgical procedure. For example, third distal taper 312 may be configured to reduce a surface area of diffuser distal end 301 which may increase a risk of unintentional trauma during a surgical procedure, e.g., reducing a surface area of diffuser distal end 301 may increase a risk of cutting a tissue during an aspiration of a surgical site. In one or more embodiments, third atraumatic offset 305 may be configured to decrease a risk of cutting a tissue during an aspiration of a surgical site, e.g., third atraumatic offset 305 may be configured to decrease a risk of cutting a tissue during an aspiration of a surgical site by increasing a surface area of diffuser distal end 301. Illustratively, third atraumatic offset 305 may have a length in a range of 0.02 to 0.04 inches, e.g., third atraumatic offset 305 may have a length of 0.03 inches. In one or more embodiments, third atraumatic offset 305 may have a length of less than 0.02 inches or greater than 0.04 inches.

Illustratively, diffuser 300 may be configured to diffuse light, e.g., diffuser 300 may be configured to diffuse light to illuminate a surgical site. In one or more embodiments, diffuser 300 may be configured to diffuse light by diffuse reflection. Illustratively, diffuser 300 may be may be manufactured from any suitable material, e.g., polymers, metals, metal alloys, etc., or from any combination of suitable materials. In one or more embodiments, diffuser 300 may be manufactured from a material configured to increase an efficiency of diffuse reflection. Illustratively, diffuser 300 may be manufactured from an optically transparent material, e.g., diffuser 300 may be manufactured from polycarbonate, acrylic, etc. In one or more embodiments, diffuser 300 may be manufactured from a material having an index of refraction that is similar to an index of refraction of optic fiber bundle 850, e.g., diffuser 300 may be manufactured from a material having an index of refraction that is not more than 10.0 to 30.0 percent less than an index of refraction of optic fiber bundle 850. Illustratively, diffuser 300 may be manufactured from a material having an index of refraction that is not more than 10.0 to 30.0 percent greater than an index of refraction of optic fiber bundle 850. In one or more embodiments, diffuser 300 may be manufactured from a material having an index of refraction that is not more than 10.0 percent less than an index of refraction of optic fiber bundle 850, e.g., diffuser 300 may be manufactured from a material having an index of refraction that is not more than 10.0 percent greater than an index of refraction of optic fiber bundle 850. Illustratively, third diffusion notch 323 may be configured to diffuse light, e.g., third diffusion notch 323 may be configured to diffuse light by diffuse reflection. In one or more embodiments, diffuser 300 may comprise a plurality of third diffusion notches 323, e.g., diffuser 300 may comprise a plurality of third diffusion notches 323 wherein each third diffusion notch 323 of the plurality of third diffusion notches 323 is configured to diffuse light. For example, a first particular third diffusion notch 323 of the plurality of third diffusion notches 323 may be configured to diffuse an incident ray of light at a first plurality of angles creating a plurality of first non-incident rays of light and a second particular third diffusion notch 323 of the plurality of third diffusion notches 323 may be configured to diffuse a first non-incident ray of light of the plurality of first non-incident rays of light at a second plurality of angles creating a plurality of second non-incident rays of light. Illustratively, diffusion taper 340 may be configured to diffuse light, e.g., diffusion taper 340 may be configured to diffuse light by diffuse reflection. For example, diffusion taper 340 may be configured to diffuse an incident ray of light at a first plurality of angles creating a plurality of first non-incident rays of light and third diffusion notch 323 may be configured to diffuse a first non-incident ray of light of the plurality of first non-incident rays of light at a second plurality of angles creating a plurality of second non-incident rays of light.

Figure 4A:
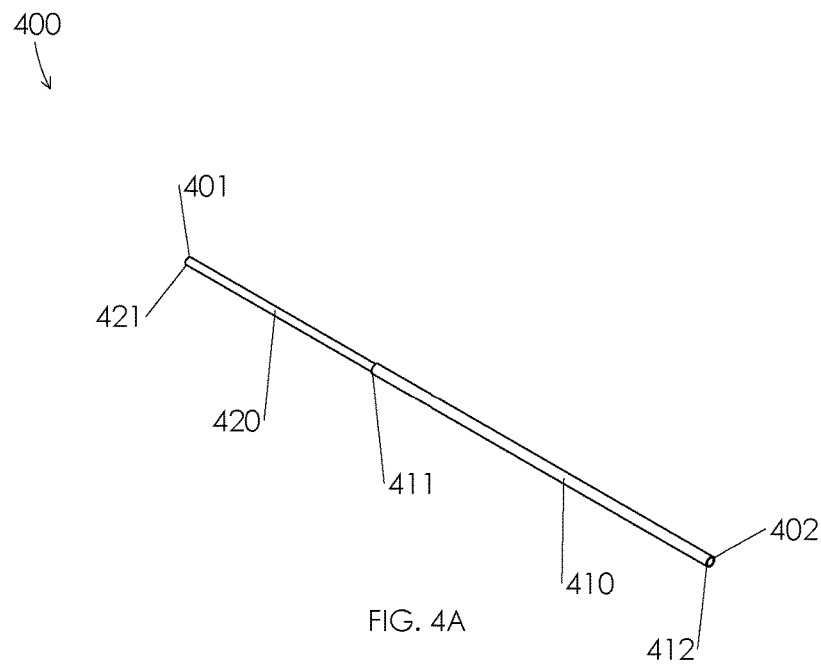
FIGS. 4A and 4B are schematic diagrams illustrating an aspiration conduit.
Figure 4B:
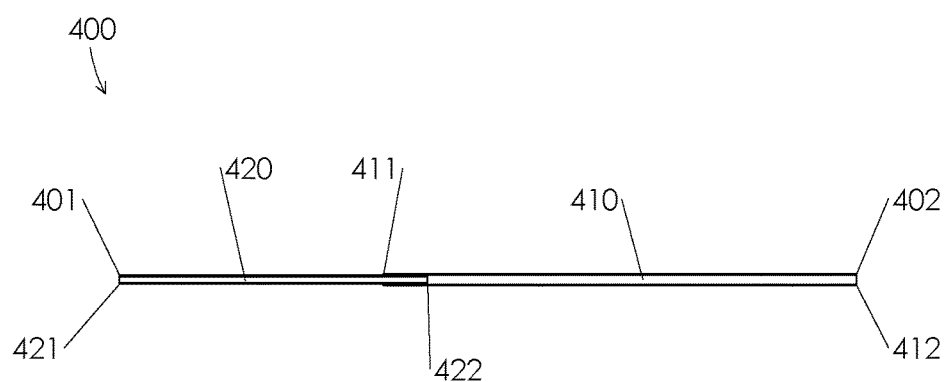

FIGS. 4A and 4B are schematic diagrams illustrating an aspiration conduit 400. FIG. 4A illustrates an isometric view of aspiration conduit 400. In one or more embodiments, aspiration conduit 400 may comprise an aspiration conduit distal end 401, an aspiration conduit proximal end 402, an outer tube 410, and an inner tube 420. FIG. 4B illustrates a cross-sectional view in a sagittal plane of aspiration conduit 400. In one or more embodiments, outer tube 410 may comprise an outer tube distal end 411 and an outer tube proximal end 412. Illustratively, inner tube 420 may comprise an inner tube distal end 421 and an inner tube proximal end 422. In one or more embodiments, a portion of inner tube 420 may be disposed within a portion of outer tube 410, e.g., inner tube proximal end 422 may be disposed within a portion of outer tube 410 where in inner tube proximal end 422 is disposed between outer tube distal end 411 and outer tube proximal end 412. Illustratively, inner tube 420 may have an outer diameter in a range of 2.0 to 10.0 Fr, e.g., inner tube 420 may have an outer diameter of 3.0 Fr. In one or more embodiments, inner tube 420 may have an outer diameter less than 2.0 Fr or greater than 10.0 Fr. Illustratively, a portion of inner tube 420 may be fixed with in a portion of outer tube 410, e.g., a portion of inner tube 420 may be fixed with in a portion of outer tube 410 by a friction fit, an adhesive, a weld, etc. In one or more embodiments, a portion of inner tube 420 may be disposed within a portion of outer tube 410 wherein inner tube distal end 421 is aspiration conduit distal end 401 and outer tube proximal end 412 is aspiration conduit proximal end 402. Illustratively, aspiration conduit 400 may be may be manufactured from any suitable material, e.g., polymers, metals, metal alloys, etc., or from any combination of suitable materials.

Figure 5A:
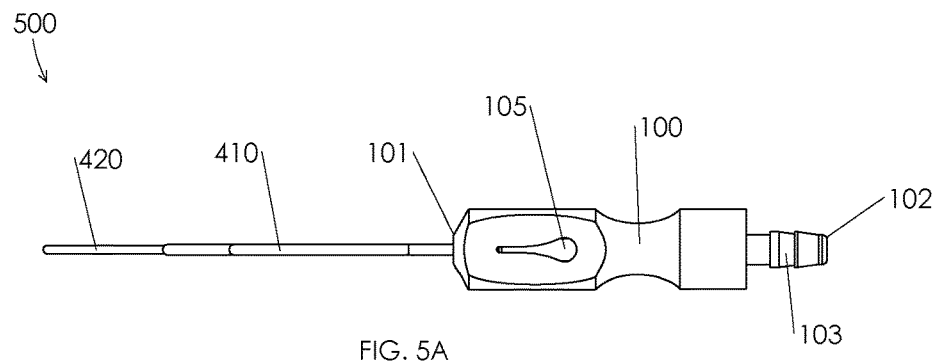
FIGS. 5A, 5B, and 5C are schematic diagrams illustrating an assembled hand-piece.
Figure 5B:
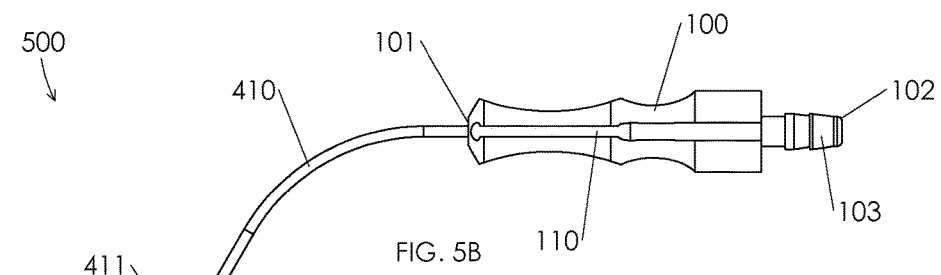
Figure 5C:
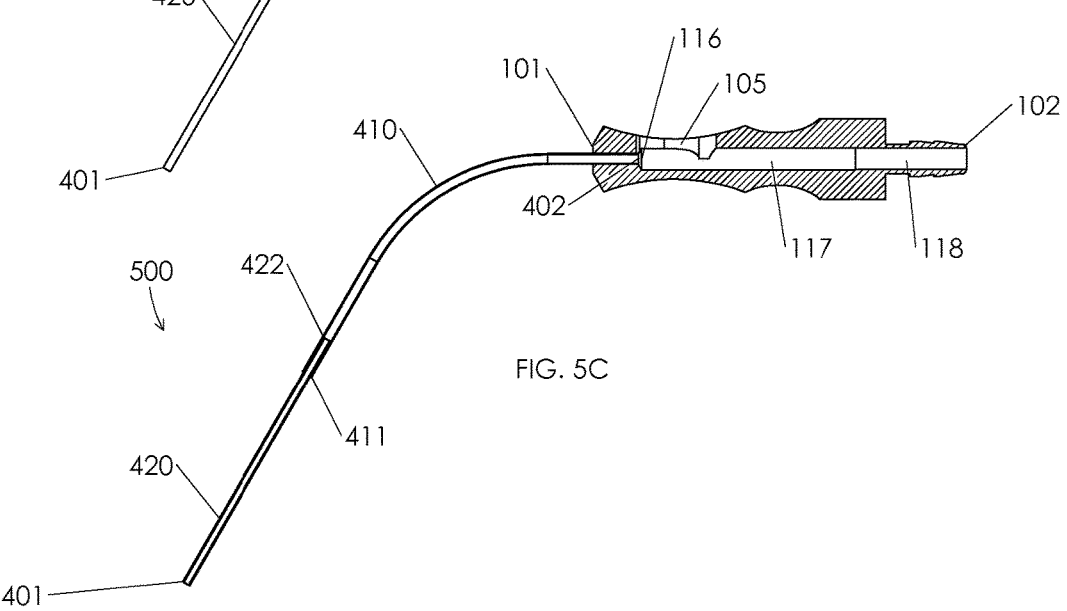

FIGS. 5A, 5B, and 5C are schematic diagrams illustrating an assembled handpiece 500. FIG. 5A illustrates a top view of assembled handpiece 500. In one or more embodiments, assembled handpiece 500 may comprise an aspiration conduit 400 and a handle 100. FIG. 5B illustrates a side view of assembled handpiece 500. Illustratively, aspiration conduit 400 may be curved wherein aspiration conduit distal end 401 is disposed inferior to aspiration conduit proximal end 402. In one or more embodiments, aspiration conduit 400 may be configured for use as a surgical retractor, e.g., aspiration conduit 400 may have a rigidity configured to retract and manipulate tissue during a surgical procedure. FIG. 5C illustrates a cross-sectional view in a sagittal plane of assembled hand-piece 500. In one or more embodiments, a portion of aspiration conduit 400 may be disposed within a portion of handle 100, e.g., aspiration conduit proximal end 402 may be disposed within handle distal chamber 115. Illustratively, a portion of aspiration conduit 400 may be disposed within a portion of handle 100 wherein aspiration conduit proximal end 402 is adjacent to handle focused taper 116. In one or more embodiments, a portion of aspiration conduit 400 may be fixed within a portion of handle 100, e.g., a portion of aspiration conduit 400 may be fixed within a portion of handle 100 by a friction fit, an adhesive, a weld, etc.

Figure 6A:
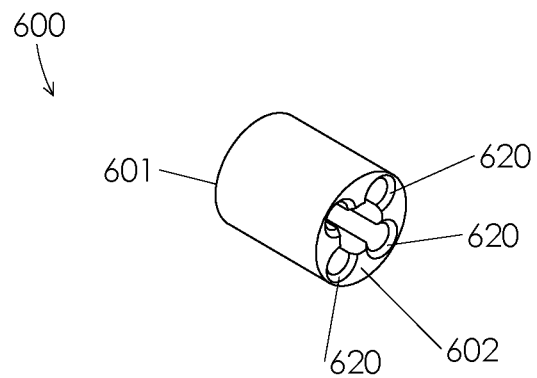
FIGS. 6A and 6B are schematic diagrams illustrating a distal retainer.
Figure 6B:
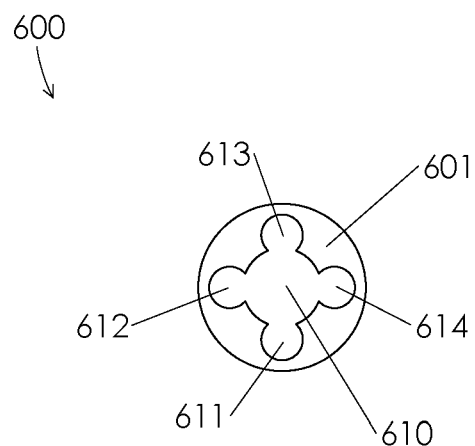

FIGS. 6A and 6B are schematic diagrams illustrating a distal retainer 600. FIG. 6A illustrates an isometric view of distal retainer 600. In one or more embodiments, distal retainer 600 may comprise a distal retainer distal end 601, a distal retainer proximal end 602, and a retaining bevel 620. FIG. 6B illustrates a front view of distal retainer 600. Illustratively, distal retainer 600 may comprise a medial bore 610, a first distal optic fiber housing 611, a second distal optic fiber housing 612, a third distal optic fiber housing 613, and a fourth distal optic fiber housing 614. In one or more embodiments, distal retainer 600 may be configured to house a portion of optic fiber bundle 850, e.g., distal retainer 600 may be configured to house optic fiber bundle distal end 851. For example, optic fiber bundle distal end 851 may be fixed within distal retainer 600, e.g., optic fiber bundle distal end 851 may be fixed within distal retainer 600 by a friction fit, an adhesive, a weld, etc. Illustratively, retaining bevel 620 may be configured to house an optic fiber as a distal end of the optic fiber expands, e.g., an optic fiber may be cleaved with a heated knife causing a distal end of the optic fiber to expand due to an application of thermal energy and retaining bevel 620 may be configured to house the optic fiber as the distal end of the optic fiber expands. In one or more embodiments, medial bore 610 may be configured to facilitate an aspiration flow, e.g., aspiration targets may be configured to flow through medial bore 610 after being aspirated out of a surgical site. In one or more embodiments, distal retainer 600 may be may be manufactured from any suitable material, e.g., polymers, metals, metal alloys, etc., or from any combination of suitable materials.

Figure 7A:
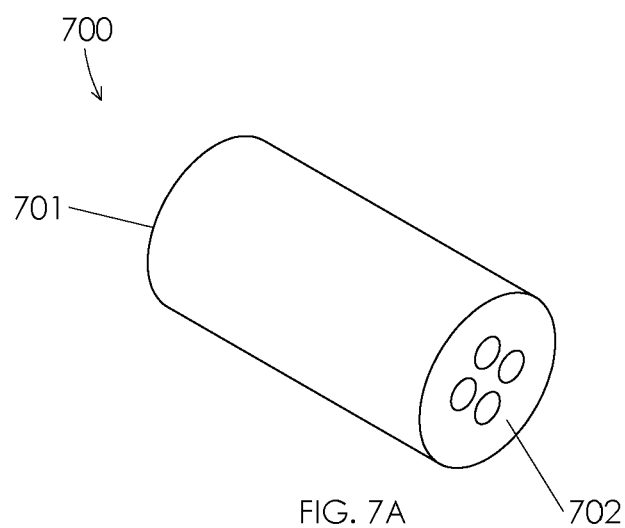
FIGS. 7A and 7B are schematic diagrams illustrating a proximal retainer.
Figure 7B:
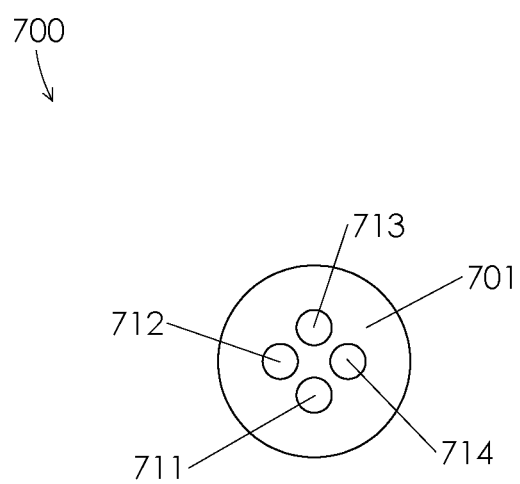

FIGS. 7A and 7B are schematic diagrams illustrating a proximal retainer 700. FIG. 7A illustrates an isometric view of proximal retainer 700. In one or more embodiments, proximal retainer 700 may comprise a proximal container distal end 701 and a proximal container proximal end 702. FIG. 7B illustrates a front view of proximal retainer 700. In one or more embodiments, proximal retainer 700 may comprise a first proximal optic fiber housing 711, a second proximal optic fiber housing 712, a third proximal optic fiber housing 713, and a fourth proximal optic fiber housing 714. Illustratively, proximal retainer 700 may be configured to house a portion of optic fiber bundle 850, e.g., proximal retainer 700 may be configured to house optic fiber bundle proximal end 852. In one or more embodiments, optic fiber bundle proximal end 852 may be fixed within proximal retainer 700, e.g., optic fiber bundle proximal end 852 may be fixed within proximal retainer 700 by a friction fit, an adhesive, a weld, etc. Illustratively, proximal retainer 700 may be may be manufactured from any suitable material, e.g., polymers, metals, metal alloys, etc., or from any combination of suitable materials.

Figure 8:
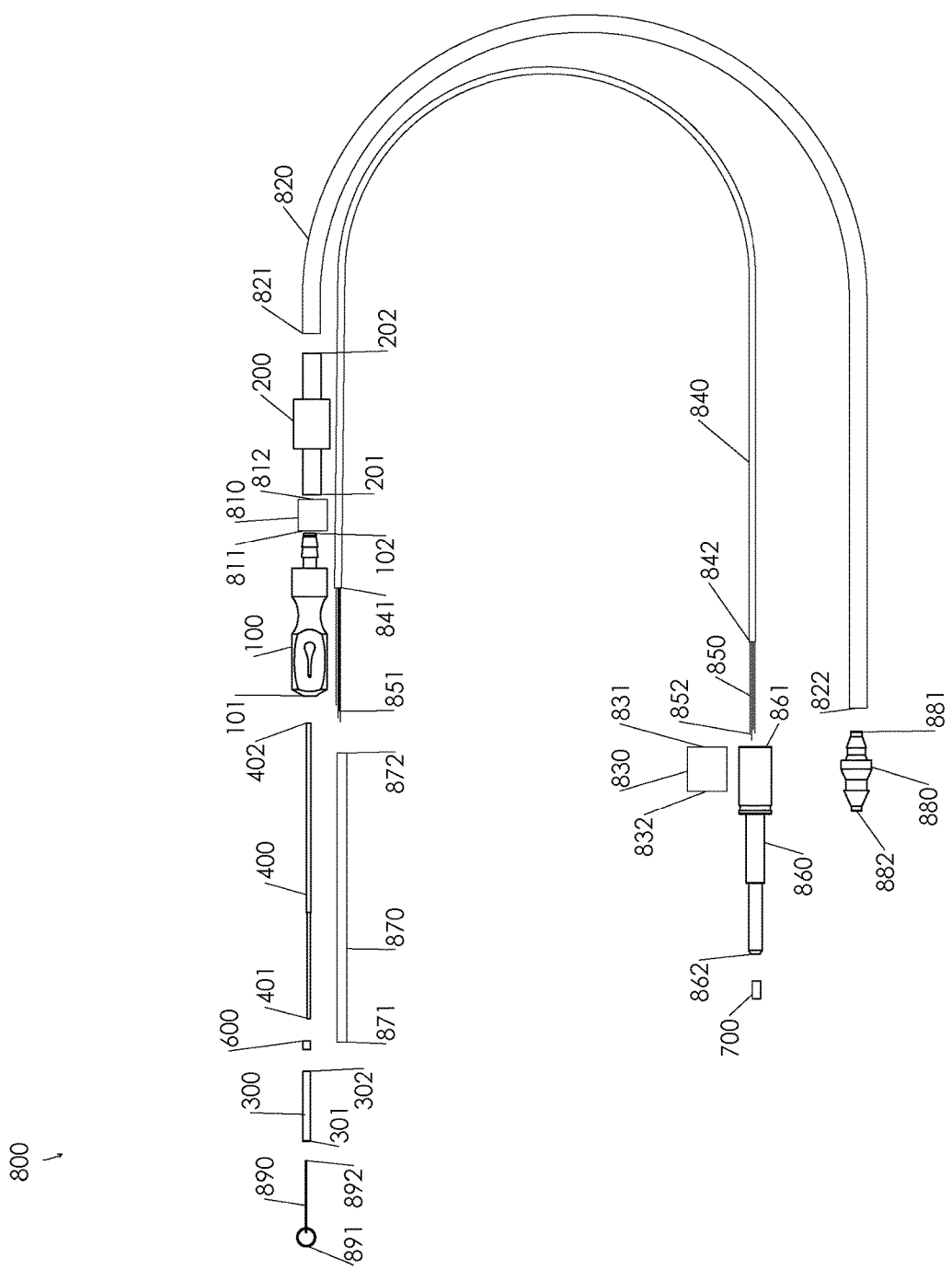
FIG. 8 is a schematic diagram illustrating an exploded view of an illuminated microsurgical probe assembly.

FIG. 8 is a schematic diagram illustrating an exploded view of an illuminated microsurgical probe assembly 800. In one or more embodiments, an illuminated microsurgical probe assembly 800 may comprise a proximal retainer 700, a light source interface 860, a proximal sleeve 830, a vacuum interface 880, an optic fiber bundle 850, an optic fiber bundle jacketing 840, an aspiration tube 820, a swivel 200, a distal sleeve 810, a handle 100, an aspiration conduit 400, a housing sleeve 870, a distal retainer 600, a diffuser 300, and a stylet 890. Illustratively, light source interface 860 may comprise a light source interface distal end 861 and a light source interface proximal end 862. In one or more embodiments, light source interface 860 may be configured to interface with a surgical illumination machine to transmit light from the surgical illumination machine through optic fiber bundle 850. Illustratively, light source interface 860 may be may be manufactured from any suitable material, e.g., polymers, metals, metal alloys, etc., or from any combination of suitable materials. In one or more embodiments, proximal sleeve 830 may comprise a proximal sleeve distal end 831 and a proximal sleeve proximal end 832. Illustratively, proximal sleeve 830 may be configured to house a portion of light source interface 860 and a portion of optic fiber bundle jacketing 840. In one or more embodiments, proximal sleeve 830 may be configured to thermally insulate a portion of light source interface 860, e.g., proximal sleeve 830 may be configured thermally insulate a user from a portion of light source interface 860. In one or more embodiments, proximal sleeve 830 may be may be manufactured from any suitable material, e.g., polymers, metals, metal alloys, etc., or from any combination of suitable materials. Illustratively, vacuum interface 880 may comprise a vacuum interface distal end 881 and a vacuum interface proximal end 882. In one or more embodiments, vacuum interface 880 may be configured to interface with a surgical vacuum machine to facilitate an aspiration of a surgical site. Illustratively, vacuum interface 880 may be may be manufactured from any suitable material, e.g., polymers, metals, metal alloys, etc., or from any combination of suitable materials.

In one or more embodiments, optic fiber bundle 850 may comprise an optic fiber bundle distal end 851 and an optic fiber bundle proximal end 852. Illustratively, optic fiber bundle 850 may be configured to transmit light from a surgical illumination machine to a surgical site, e.g., light from a surgical illumination machine may ingress optic fiber bundle 850 at optic fiber bundle distal end 852 and light from a surgical illumination machine may egress optic fiber bundle 850 at optic fiber bundle distal end 851. In one or more embodiments, optic fiber bundle 850 may comprise a single optic fiber. Illustratively, optic fiber bundle 850 may comprise a plurality of optic fibers. In one or more embodiments, optic fiber bundle 850 may comprise a number of optic fibers in a range of 2 to 20, e.g., optic fiber bundle 850 may comprise 4 optic fibers. Illustratively, optic fiber bundle 850 may comprise less than 2 optic fibers or greater than 20 optic fibers. In one or more embodiments, optic fiber bundle 850 may comprise at least 2 optic fibers but less than 20 optic fibers. For example, optic fiber bundle 850 may comprise 3 optic fibers. In one or more embodiments, optic fiber bundle 850 may comprise one or more optic fibers manufactured from glass, e.g., optic fiber bundle 850 may comprise one or more optic fibers manufactured from silica. Illustratively, optic fiber bundle 850 may comprise one or more optic fibers manufactured from plastic, e.g., optic fiber bundle 850 may comprise one or more optic fibers manufactured from Polymethyl Methacrylate Resin, Polystyrene, etc. In one or more embodiments, optic fiber bundle 850 may comprise one or more optic fibers having a cladding material, e.g., optic fiber bundle 850 may comprise one or more optic fibers having a cladding material manufactured from a fluorinated polymer, a silicone resin, etc. Illustratively, optic fiber bundle 850 may comprise one or more optic fibers having a step index refractive index profile. In one or more embodiments, optic fiber bundle 850 may comprise one or more multi-mode optic fibers, one or more single-mode optic fibers, etc. In one or more embodiments, optic fiber bundle 850 may comprise one or more optic fibers having a core refractive index in a range of 1.3 to 1.8, e.g., optic fiber bundle 850 may comprise one or more optic fibers having a core refractive index of 1.49. Illustratively, optic fiber bundle 850 may comprise one or more optic fibers having a core refractive index of less than 1.3 or greater than 1.8. In one or more embodiments, optic fiber bundle 850 may comprise one or more optic fibers having a numerical aperture in a range of 0.3 to 0.8, e.g., optic fiber bundle 850 may comprise one or more optic fibers having a numerical aperture of 0.5. In one or more embodiments, optic fiber bundle 850 may comprise one or more optic fibers having a numerical aperture of less than 0.3 or greater than 0.8. Illustratively, optic fiber bundle 850 may comprise one or more optic fibers having a core diameter in a range of 185 to 785 micrometers, e.g., optic fiber bundle 850 may comprise one or more optic fibers having a core diameter of 485 micrometers. In one or more embodiments, optic fiber bundle 850 may comprise one or more optic fibers having a core diameter of less than 185 micrometers or greater than 785 micrometers. Illustratively, optic fiber bundle 850 may comprise one or more optic fibers having an overall diameter in a range of 200 to 800 micrometers, e.g., optic fiber bundle 850 may comprise one or more optic fiber having an overall diameter of 500 micrometers. In one or more embodiments, optic fiber bundle 850 may comprise one or more optic fibers having an overall diameter of less than 200 or greater than 800 micrometers.

In one or more embodiments, optic fiber bundle jacketing 840 may comprise an optic fiber bundle jacketing distal end 841 and an optic fiber bundle jacketing proximal end 842. Illustratively, optic fiber bundle jacketing 840 may be configured to house optic fiber bundle 850, e.g., optic fiber bundle jacketing 840 may be configured to protect optic fiber bundle 850 from external forces during a surgical procedure. In one or more embodiments, optic fiber bundle jacketing 840 may be may be manufactured from any suitable material, e.g., polymers, metals, metal alloys, etc., or from any combination of suitable materials. Illustratively, aspiration tube 820 may comprise an aspiration tube distal end 821 and an aspiration tube proximal end 822. In one or more embodiments, aspiration tube 820 may be configured to facilitate an aspiration of a surgical site. Illustratively, aspiration tube 820 may be may be manufactured from any suitable material, e.g., polymers, metals, metal alloys, etc., or from any combination of suitable materials. In one or more embodiments, distal sleeve 810 may comprise a distal sleeve distal end 811 and a distal sleeve proximal end 812. Illustratively, distal sleeve 810 may be configured to interface with a portion of handle 100 and a portion of swivel 200, e.g., distal sleeve 810 may be configured to interface with handle proximal end 102 and swivel distal end 201. In one or more embodiments, distal sleeve 810 may be configured to facilitate an aspiration of a surgical site. Illustratively, distal sleeve 810 may be may be manufactured from any suitable material, e.g., polymers, metals, metal alloys, etc., or from any combination of suitable materials.

In one or more embodiments, housing sleeve 870 may comprise a housing sleeve distal end 871 and a housing sleeve proximal end 872. Illustratively, housing sleeve 870 may be configured to house optic fiber bundle 850, optic fiber bundle jacketing 840, aspiration conduit 400, distal retainer 600, and diffuser 300. In one or more embodiments, a portion of housing sleeve 870 may be configured to facilitate an aspiration of a surgical site. Illustratively, housing sleeve 870 may be may be manufactured from any suitable material, e.g., polymers, metals, metal alloys, etc., or from any combination of suitable materials. In one or more embodiments, stylet 890 may comprise a stylet distal end 891 and a stylet proximal end 892. Illustratively, a portion of stylet 890 may comprise a loop, e.g., stylet distal end 891 may comprise a loop. In one or more embodiments, stylet 890 may be configured to remove debris obstructing an aspiration flow within aspiration conduit 400. For example, aspiration conduit 400 may be configured to aspirate blood, surgical irrigation fluids, and tissue from a surgical site. Illustratively, blood clots and tissue may accumulate within aspiration conduit 400 reducing an aspiration flow rate at a surgical site. In one or more embodiments, stylet 890 may be configured to breakup accumulated debris within aspiration conduit 400, e.g., stylet proximal end 892 may be configured to breakup accumulated blood clots and tissue within aspiration conduit 400. Illustratively, stylet 890 may be manufactured from any suitable material, e.g., polymers, metals, metal alloys, etc., or from any combination of suitable materials.

FIG. 9 is a schematic diagram illustrating an assembled illuminated microsurgical probe 900. In one or more embodiments, an assembled illuminated microsurgical probe 900 may comprise a proximal retainer 700, a light source interface 860, a proximal sleeve 830, a vacuum interface 880, an optic fiber bundle 850, an optic fiber bundle jacketing 840, an aspiration tube 820, a swivel 200, a distal sleeve 810, a handle 100, an aspiration conduit 400, a housing sleeve 870, a distal retainer 600, a diffuser 300, and a stylet 890. Illustratively, a portion of proximal retainer 700 may be disposed within a portion of light source interface 860, e.g., a portion of proximal retainer 700 may be disposed within light source interface proximal end 862. In one or more embodiments, a portion of proximal retainer 700 may be fixed within a portion of light source interface 860, e.g., a portion of proximal retainer 700 may be fixed within a portion of light source interface 860 by a friction fit, an adhesive, a weld, etc. In one or more embodiments, a first portion of proximal retainer 700 may be fixed within a portion of light source interface 860 wherein a second portion of proximal retainer 700 extends from light source interface proximal end 862. Illustratively, a portion of distal retainer 600 may be disposed within a portion of diffuser 300, e.g., a portion of distal retainer 600 may be disposed within diffuser proximal end 302. In one or more embodiments, a portion of distal retainer 600 may be disposed within a portion of diffuser 300 wherein distal retainer distal end 601 is disposed between diffuser distal end 301 and diffuser proximal end 302, e.g., a portion of distal retainer 600 may be disposed within diffuser 300 wherein distal retainer proximal end 602 is proximal to diffuser proximal end 302. Illustratively, distal retainer 600 may be disposed within diffuser 300 wherein distal retainer distal end 601 is disposed between diffuser distal end 301 and diffuser proximal end 302, e.g., distal retainer 600 may be disposed within diffuser 300 wherein distal retainer proximal end 602 is disposed between diffuser distal end 301 and diffuser proximal end 302. In one or more embodiments, a portion of distal retainer 600 may be fixed within a portion of diffuser 300, e.g., a portion of distal retainer 600 may be fixed within a portion of diffuser 300 by a friction fit, an adhesive, a weld, etc. Illustratively, proximal sleeve 830 may be disposed over a portion of light source interface 860, e.g., proximal sleeve 830 may be disposed over light source interface distal end 861. In one or more embodiments, proximal sleeve 830 may be fixed to a portion of light source interface 860, e.g., proximal sleeve 830 may be fixed to a portion of light source interface 860 by a force of friction, an adhesive, etc.

Illustratively, optic fiber bundle 850 may be disposed in proximal retainer 700, light source interface 860, optic fiber bundle jacketing 840, optic fiber bundle jacketing housing 110, housing sleeve 870, distal retainer 600, and diffuser 300. In one or more embodiments, optic fiber bundle 850 may be disposed in optic fiber bundle jacketing 840 wherein a portion of optic fiber bundle 850 extends a distance from optic fiber bundle jacketing proximal end 842, e.g., optic fiber bundle 850 may be disposed in optic fiber bundle jacketing 840 wherein optic fiber bundle proximal end 852 extends a distance from optic fiber bundle jacketing proximal end 842. Illustratively, optic fiber bundle 850 may be disposed in optic fiber bundle jacketing 840 wherein a portion of optic fiber bundle 850 extends a distance from optic fiber bundle jacketing distal end 841, e.g., optic fiber bundle 850 may be disposed in optic fiber bundle jacketing 840 wherein optic fiber bundle distal end 851 extends a distance from optic fiber bundle jacketing distal end 841.

In one or more embodiments, optic fiber bundle 850 may be disposed in optic fiber bundle jacketing 840 wherein a portion of optic fiber bundle 850 is disposed in optic fiber bundle jacketing housing 110, e.g., a portion of optic fiber bundle jacketing 840 may be disposed in optic fiber bundle jacketing housing 110. Illustratively, optic fiber bundle jacketing 840 may be disposed within optic fiber bundle jacketing housing 110 wherein a portion of optic fiber jacketing 840 extends out from optic fiber bundle jacketing housing distal end 111, e.g., optic fiber bundle jacketing 840 may be disposed within optic fiber bundle jacketing housing 110 wherein optic fiber jacketing distal end 841 extends out from optic fiber bundle jacketing housing distal end 111. In one or more embodiments, optic fiber bundle jacketing 840 may be disposed within optic fiber bundle jacketing housing 110 wherein a portion of optic fiber jacketing 840 extends out from optic fiber bundle jacketing housing proximal end 112, e.g., optic fiber bundle jacketing 840 may be disposed within optic fiber bundle jacketing housing 110 wherein optic fiber jacketing proximal end 842 extends out from optic fiber bundle jacketing housing proximal end 112.

In one or more embodiments, optic fiber bundle 850 may be disposed in light source interface 860 wherein a portion of optic fiber bundle 850 is disposed in proximal retainer 700, e.g., optic fiber bundle 850 may be disposed in light source interface 860 wherein optic fiber bundle proximal end 852 is disposed in proximal retainer 700. Illustratively, optic fiber bundle 850 may be disposed in light source interface 860 wherein one or more optic fibers of optic fiber bundle 850 may be disposed in first proximal optic fiber housing 711. In one or more embodiments, optic fiber bundle 850 may be disposed in light source interface 860 wherein one or more optic fibers of optic fiber bundle 850 may be fixed within first proximal optic fiber housing 711, e.g., one or more optic fibers of optic fiber bundle 850 may be fixed within first proximal optic fiber housing 711 by a force of friction, an adhesive, a crimp, etc. Illustratively, optic fiber bundle 850 may be disposed in light source interface 860 wherein one or more optic fibers of optic fiber bundle 850 may be disposed in second proximal optic fiber housing 712. In one or more embodiments, optic fiber bundle 850 may be disposed in light source interface 860 wherein one or more optic fibers of optic fiber bundle 850 may be fixed within second proximal optic fiber housing 712, e.g., one or more optic fibers of optic fiber bundle 850 may be fixed within second proximal optic fiber housing 712 by a force of friction, an adhesive, a crimp, etc. Illustratively, optic fiber bundle 850 may be disposed in light source interface 860 wherein one or more optic fibers of optic fiber bundle 850 may be disposed in third proximal optic fiber housing 713. In one or more embodiments, optic fiber bundle 850 may be disposed in light source interface 860 wherein one or more optic fibers of optic fiber bundle 850 may be fixed within third proximal optic fiber housing 713, e.g., one or more optic fibers of optic fiber bundle 850 may be fixed within third proximal optic fiber housing 713 by a force of friction, an adhesive, a crimp, etc. Illustratively, optic fiber bundle 850 may be disposed in light source interface 860 wherein one or more optic fibers of optic fiber bundle 850 may be disposed in fourth proximal optic fiber housing 714. In one or more embodiments, optic fiber bundle 850 may be disposed in light source interface 860 wherein one or more optic fibers of optic fiber bundle 850 may be fixed within fourth proximal optic fiber housing 714, e.g., one or more optic fibers of optic fiber bundle 850 may be fixed within fourth proximal optic fiber housing 714 by a force of friction, an adhesive, a crimp, etc.

Illustratively, optic fiber bundle 850 may be disposed in housing sleeve 870, e.g., optic fiber bundle 850 may ingress housing sleeve 870 at housing sleeve opening 910. In one or more embodiments, optic fiber bundle 850 may be disposed in housing sleeve 870 wherein a portion of optic fiber bundle 850 is disposed in distal retainer 600, e.g., optic fiber bundle 850 may be disposed in housing sleeve 870 wherein optic fiber bundle distal end 851 is disposed in distal retainer 600. Illustratively, optic fiber bundle 850 may be disposed in housing sleeve 870 wherein one or more optic fibers of optic fiber bundle 850 may be disposed in first distal optic fiber housing 611. In one or more embodiments, optic fiber bundle 850 may be disposed in housing sleeve 870 wherein one or more optic fibers of optic fiber bundle 850 may be fixed within first distal optic fiber housing 611, e.g., one or more optic fibers of optic fiber bundle 850 may be fixed within first distal optic fiber housing 611 by a force of friction, an adhesive, a crimp, etc. Illustratively, optic fiber bundle 850 may be disposed in housing sleeve 870 wherein one or more optic fibers of optic fiber bundle 850 may be disposed in second distal optic fiber housing 612. In one or more embodiments, optic fiber bundle 850 may be disposed in housing sleeve 870 wherein one or more optic fibers of optic fiber bundle 850 may be fixed within second distal optic fiber housing 612, e.g., one or more optic fibers of optic fiber bundle 850 may be fixed within second distal optic fiber housing 612 by a force of friction, an adhesive, a crimp, etc. Illustratively, optic fiber bundle 850 may be disposed in housing sleeve 870 wherein one or more optic fibers of optic fiber bundle 850 may be disposed in third distal optic fiber housing 613. In one or more embodiments, optic fiber bundle 850 may be disposed in housing sleeve 870 wherein one or more optic fibers of optic fiber bundle 850 may be fixed within third distal optic fiber housing 613, e.g., one or more optic fibers of optic fiber bundle 850 may be fixed within third distal optic fiber housing 613 by a force of friction, an adhesive, a crimp, etc. Illustratively, optic fiber bundle 850 may be disposed in housing sleeve 870 wherein one or more optic fibers of optic fiber bundle 850 may be disposed in fourth distal optic fiber housing 614. In one or more embodiments, optic fiber bundle 850 may be disposed in housing sleeve 870 wherein one or more optic fibers of optic fiber bundle 850 may be fixed within fourth distal optic fiber housing 614, e.g., one or more optic fibers of optic fiber bundle 850 may be fixed within fourth distal optic fiber housing 614 by a force of friction, an adhesive, a crimp, etc.

Illustratively, aspiration conduit 400 may be disposed in handle 100 and in housing sleeve 870. In one or more embodiments, aspiration conduit 400 may be disposed in housing sleeve 870 wherein a portion of aspiration conduit 400 is disposed in distal retainer 600, e.g., aspiration conduit 400 may be disposed in housing sleeve 870 wherein aspiration conduit distal end 401 is disposed in medial bore 610. Illustratively, aspiration conduit 400 may be disposed in housing sleeve 870 wherein a portion of aspiration conduit is fixed within a portion of distal retainer 600, e.g., aspiration conduit 400 may be disposed in housing sleeve 870 wherein aspiration conduit distal end 401 is fixed within medial bore 610 by a friction fit, an adhesive, a weld, etc. In one or more embodiments, aspiration conduit 400 may be disposed in housing sleeve 870 wherein a portion of aspiration conduit is disposed in diffuser 300, e.g., aspiration conduit 400 may be disposed in housing sleeve 870 wherein aspiration conduit distal end 401 is disposed in diffuser inner bore 315. Illustratively, aspiration conduit 400 may be disposed in diffuser 300 wherein aspiration conduit distal end 401 is disposed between diffuser distal end 301 and distal proximal end 302. In one or more embodiments, aspiration conduit 400 may be disposed in diffuser 300 wherein aspiration conduit distal end 401 is adjacent to first atraumatic offset 303. Illustratively, aspiration conduit 400 may be disposed in diffuser 300 wherein aspiration conduit distal end 401 is adjacent to second atraumatic offset 304. In one or more embodiments, aspiration conduit 400 may be disposed in diffuser 300 wherein aspiration conduit distal end 401 is adjacent to third atraumatic offset 305. Illustratively, aspiration conduit 400 may be disposed in housing sleeve 870 wherein a portion of aspiration conduit 400 may be fixed within a portion of diffuser 300, e.g., aspiration conduit 400 may be disposed in housing sleeve 870 wherein aspiration conduit distal end 401 is fixed within diffuser inner bore 315 by a friction fit, an adhesive, a weld, etc. In one or more embodiments, optic fiber bundle 850 may be disposed in aspiration conduit 400, e.g., optic fiber bundle 850 may be disposed in aspiration conduit 400 wherein optic fiber bundle distal end 850 extends a distance from conduit distal end 401. Illustratively, optic fiber bundle 850 may be disposed in housing sleeve 870 and not disposed in aspiration conduit 400, e.g., optic fiber bundle 850 may be disposed in housing sleeve 870 wherein a portion of optic fiber bundle 850 is adjacent to a portion of aspiration conduit 400.

In one or more embodiments, a portion of handle 100 may be disposed in a portion of distal sleeve 810, e.g., a portion of handle 100 may be disposed in in a portion of distal sleeve 810 wherein handle proximal end 102 is disposed in distal sleeve distal end 811. Illustratively, a portion of handle 100 may be disposed in a portion of distal sleeve 810 wherein barb 103 is disposed in distal sleeve distal end 811. For example, barb 103 may comprise a luer fitting and a portion of distal sleeve 810 may be configured to attach by barb 103 by a luer lock. In one or more embodiments, a portion of handle 100 may be fixed within distal sleeve 810, e.g., handle proximal end 102 may be fixed within distal sleeve 810 by a force of friction, a tie, a crimp, an adhesive, etc. Illustratively, a portion of handle 100 may be disposed in a portion of distal sleeve 810 wherein distal sleeve distal end 811 is adjacent to distal sleeve interface 104, e.g., a portion of handle 100 may be disposed in a portion of distal sleeve 810 wherein distal sleeve distal end 811 is fixed to distal sleeve interface 104 by an adhesive, a weld, etc. In one or more embodiments, a portion of handle 100 may be disposed in a portion of distal sleeve 810 wherein a portion of handle proximal chamber 118 is disposed in distal sleeve 810, e.g., a portion of handle 100 may be disposed in a portion of distal sleeve 810 wherein a portion of handle proximal chamber 118 is disposed in distal sleeve distal end 811.

Illustratively, a portion of swivel 200 may be disposed in a portion of distal sleeve 810, e.g., swivel distal end 201 may be disposed in distal sleeve proximal end 812. In one or more embodiments, a portion of swivel 200 may be disposed in a portion of distal sleeve 810 wherein a portion of outer swivel component 210 is disposed in a portion of distal sleeve 810, e.g., a portion of swivel 200 may be disposed in a portion of distal sleeve 810 wherein outer swivel component distal end 211 is disposed in distal sleeve proximal end 812. Illustratively, a portion of swivel 200 may be fixed within a portion of distal sleeve 810, e.g., a portion of swivel 200 may be fixed within a portion of distal sleeve 810 by a force of friction, an adhesive, a crimp, etc. In one or more embodiments, a portion of swivel 200 may be disposed in a portion of distal sleeve 810 wherein a portion of outer swivel component inner bore 215 is disposed in a portion of distal sleeve 810. Illustratively, a portion of swivel 200 may be disposed in a portion of aspiration tube 820, e.g., swivel proximal end 202 may be disposed in aspiration tube distal end 821. In one or more embodiments, a portion of swivel 200 may be disposed in a portion of aspiration tube 820 wherein a portion of inner swivel component 220 is disposed in a portion of aspiration tube 820, e.g., a portion of swivel 200 may be disposed in a portion of aspiration tube 820 wherein inner swivel component proximal end 222 is disposed in aspiration tube distal end 821. Illustratively, a portion of swivel 200 may be fixed within a portion of aspiration tube 820, e.g., a portion of swivel 200 may be fixed within a portion of aspiration tube 820 by a force of friction, an adhesive, a crimp, etc. In one or more embodiments, a portion of swivel 200 may be disposed in a portion of aspiration tube 820 wherein a portion of inner swivel component inner bore 225 is disposed in a portion of aspiration tube 820.

Illustratively, a portion of vacuum interface 880 may be disposed in a portion of aspiration tube 820, e.g., vacuum interface distal end 881 may be disposed in aspiration tube proximal end 822. In one or more embodiments, a portion of vacuum interface 880 may be fixed within a portion of aspiration tube 820, e.g., a portion of vacuum interface 880 may be fixed within a portion of aspiration tube 820 by a force of friction, an adhesive, a crimp, etc. Illustratively, a portion of aspiration conduit 400 may be disposed in a portion of diffuser 300, e.g., aspiration conduit distal end 401 may be disposed in diffuser proximal end 302. In one or more embodiments, aspiration conduit 400 may be disposed in diffuser 300 and in distal retainer 600, e.g., aspiration conduit 400 may be disposed in diffuser inner bore 315 and medial bore 610. Illustratively, a portion of aspiration conduit 400 may be fixed within a portion of diffuser 300, e.g., a portion of aspiration conduit 400 may be fixed within a portion of diffuser 300 by an adhesive, a friction fit, a set-screw, etc. In one or more embodiments, a portion of aspiration conduit 400 may be fixed within a portion of distal retainer 600, e.g., a portion of aspiration conduit 400 may be fixed within a portion of distal retainer 600 by an adhesive, a friction fit, a setscrew, etc. Illustratively, a portion of stylet 890 may be disposed in diffuser 300, distal retainer 600, and aspiration conduit 400, e.g., a portion of stylet 890 may be disposed in diffuser inner bore 315, medial bore 610, and aspiration conduit distal end 401. In one or more embodiments, stylet 890 may not be fixed within diffuser 300, distal retainer 600, or aspiration conduit 400, e.g., stylet 890 may be removable from diffuser inner bore 315, medial bore 610, and aspiration conduit 400.

In one or more embodiments, assembled illuminated microsurgical probe 900 may be configured to remove an aspiration target, e.g., blood, irrigation fluid, bone, tissue, etc., from a surgical site. Illustratively, vacuum interface 880 may be configured to interface with a surgical vacuum machine to decrease a pressure within aspiration tube 820. In one or more embodiments, decreasing a pressure within aspiration tube 820 may be configured to decrease a pressure within swivel 200. Illustratively, decreasing a pressure within swivel 200 may be configured to decrease a pressure within distal sleeve 810. In one or more embodiments, decreasing a pressure within distal sleeve 810 may be configured to decrease a pressure within handle 100. Illustratively, decreasing a pressure within handle 100 may be configured to decrease a pressure within aspiration conduit 400. In one or more embodiments, decreasing a pressure within aspiration conduit 400 may be configured to decrease a pressure within diffuser 300. Illustratively, decreasing a pressure within diffuser 300 may be configured to remove an aspiration target from a surgical site.

In one or more embodiments, a surgeon may manipulate assembled illuminated microsurgical probe 900 to actuate diffuser distal end 301 towards an aspiration target during a surgical procedure. Illustratively, vacuum interface 880 may be configured to interface with a surgical vacuum machine to decrease a pressure within diffuser 300 wherein the pressure within diffuser 300 is less than an ambient pressure in a surgical site. In one or more embodiments, a pressure within diffuser 300 may be configured to cause the aspiration target to egress the surgical site and ingress diffuser inner bore 315. In one or more embodiments, a pressure within aspiration conduit 400 may be configured to cause the aspiration target to egress diffuser inner bore 315 and ingress aspiration conduit 400. Illustratively, a pressure within handle 100 may be configured to cause the aspiration target to egress aspiration conduit 400 and ingress handle distal chamber 115. In one or more embodiments, a pressure within handle inner bore 117 may be configured to cause the aspiration target to egress handle distal chamber 115 and ingress handle inner bore 117. Illustratively, a pressure within handle proximal chamber 118 may be configured to cause the aspiration target to egress handle inner bore 117 and ingress handle proximal chamber 118. In one or more embodiments, a pressure within distal sleeve 810 may be configured to cause the aspiration target to egress handle proximal chamber 118 and ingress distal sleeve 810. Illustratively, a pressure within swivel 200 may be configured to cause the aspiration target to egress distal sleeve 810 and ingress outer swivel component inner bore 215. In one or more embodiments, a pressure within inner swivel component inner bore 225 may be configured to cause the aspiration target to egress outer swivel component inner bore 215 and ingress inner swivel component inner bore 225. Illustratively, a pressure within aspiration tube 820 may be configured to cause the aspiration target to egress inner swivel component inner bore 225 and ingress aspiration tube 820.

In one or more embodiments, swivel 200 may be configured to prevent a torqueing of aspiration tube 820, e.g., a surgeon may rotate handle 100 about a medial axis of handle 100 without torqueing aspiration tube 820. Illustratively, swivel 200 may be configured to rotate outer swivel component 210 relative to inner swivel component 220 in response to a rotation of handle 100 about a medial axis of handle 100, e.g., swivel 200 may be configured to rotate inner swivel component 220 relative to outer swivel component 210 in response to a rotation of handle 100 about a medial axis of handle 100. In one or more embodiments, swivel 200 may be configured to prevent a torqueing of aspiration tube 820 without decreasing an aspiration flow rate between handle 100 and aspiration tube 820, e.g., swivel 200 may be configured to prevent a torqueing of aspiration tube 820 without increasing an aspiration flow rate between handle 100 and aspiration tube 820.

Illustratively, a surgeon may manipulate an aspiration flow rate of assembled illuminated microsurgical probe 900, e.g., a surgeon may manipulate an aspiration flow rate of assembled illuminated microsurgical probe 900 by modifying one or more settings of a surgical vacuum machine. In one or more embodiments, a surgeon may manipulate an aspiration flow rate of assembled illuminated microsurgical probe 900 by selectively closing vent 105, e.g., a surgeon may manipulate an aspiration flow rate of assembled illuminated microsurgical probe 900 by selectively opening vent 105. Illustratively, vent 105 is normally open. In one or more embodiments, a surgeon may partially close vent 105 by partially covering vent 105, e.g., a surgeon may partially close vent 105 by partially covering vent 105 with the surgeon's thumb, finger, palm, etc. Illustratively, a surgeon my fully close vent 105 by fully covering vent 105, e.g., a surgeon may fully close vent 105 by fully covering vent 105 with the surgeon's thumb, finger, palm, etc. In one or more embodiments, vacuum interface 880 may be configured to interface with a surgical vacuum machine to decrease a pressure within handle 100 wherein the pressure with-in handle 100 is less than an ambient pressure in a surgical site. Illustratively, a surgeon may increase a pressure within handle 100 by opening vent 105, e.g., a surgeon my increase a pressure within handle 100 by uncovering a covered portion of vent 105. In one or more embodiments, increasing a pressure within handle 100 may be configured to decrease an aspiration flow rate of assembled illuminated microsurgical probe 900, e.g., a surgeon may decrease an aspiration flow rate of assembled illuminated microsurgical probe 900 by uncovering a covered portion of vent 105. Illustratively, a surgeon may decrease a pressure within handle 100 by closing vent 105, e.g., a surgeon may decrease a pressure within handle 100 by covering an uncovered portion of vent 105. In one or more embodiments, decreasing a pressure within handle 100 may be configured to increase an aspiration flow rate of assembled illuminated microsurgical probe 900, e.g., a surgeon may increase an aspiration flow rate of assembled illuminated microsurgical probe 900 by covering an uncovered portion of vent 105.

In one or more embodiments, assembled illuminated microsurgical probe 900 may be configured to illuminate a surgical site. Illustratively, optic fiber bundle 850 may be configured to receive light from a surgical illumination machine, e.g., optic fiber bundle proximal end 852 may be configured to receive light from a surgical illumination machine. In one or more embodiments, optic fiber bundle 850 may be configured to transmit light from a surgical illumination machine to diffuser 300, e.g., optic fiber bundle distal end 851 may be configured to deliver light from a surgical illumination machine to diffuser 300. Illustratively, diffuser 300 may be configured to diffuse light from a surgical illumination machine to illuminate a surgical site. In one or more embodiments, a surgical illumination machine may comprise a standard endoscopy light source. For example, a surgical illumination machine may comprise a light source intended for use with an endoscope in endoscopy procedures. In one or more embodiments, an inner portion of optic fiber bundle jacketing 840 may comprise a reflective surface configured to reflect light. Illustratively, an inner portion of housing sleeve 870 may comprise a reflective surface configured to reflect light. In one or more embodiments, assembled illuminated microsurgical probe 900 may be configured to illuminate a surgical site wherein diffuser 300 emits at least 25.0 lumens. Illustratively, assembled illuminated microsurgical probe 900 may be configured to illuminate a surgical site wherein a temperature of diffuser 300 does not exceed 74.0 degrees Fahrenheit. In one or more embodiments, assembled illuminated microsurgical probe 900 may be configured to illuminate a surgical site wherein diffuser 300 emits at least 25.0 lumens and wherein a temperature of diffuser 300 does not exceed 74.0 degrees Fahrenheit. Illustratively, assembled illuminated microsurgical probe 900 may be configured to illuminate a surgical site wherein diffuser 300 emits in a range of 20.0 to 75.0 lumens, e.g., assembled illuminated microsurgical probe 900 may be configured to illuminate a surgical site wherein diffuser 300 emits 50.0 lumens. In one or more embodiments, assembled illuminated microsurgical probe 900 may be configured to illuminate a surgical site wherein diffuser 300 emits less than 20.0 lumens or greater than 75.0 lumens.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of an illuminated microsurgical probe, the teachings of the present invention are equally suitable to any systems where the functionality may be employed. Therefore, it is the object of the appended claims to cover all such variations and modifications as come within the true spirit and scope of the invention.

What is claimed is:

1. An instrument comprising:
    a handle having a handle distal end and a handle proximal end;
    an inner bore of the handle, the inner bore extending from the handle distal end to the handle proximal end;
    a diffuser having a diffuser distal end, a diffuser proximal end, and a diffuser inner bore;
    an aspiration conduit having an aspiration conduit distal end and an aspiration conduit proximal end wherein the aspiration conduit distal end is disposed in the diffuser inner bore and the aspiration conduit proximal end is disposed in the inner bore of the handle; and
    an optic fiber bundle having an optic fiber bundle distal end and an optic fiber bundle proximal end, the optic fiber distal end disposed in the diffuser inner bore.

2. The instrument of claim 1 further comprising:
    a vent of the handle having a vent distal end and a vent proximal end, the vent configured to manipulate a pressure within the handle inner bore.

3. The instrument of claim 1 further comprising:
a light source interface having a light source interface distal end and a light source interface proximal end, the light source configured to interface with a surgical illumination machine.

4. The instrument of claim 3 further comprising:
a proximal retainer having a proximal retainer distal end and a proximal retainer proximal end, the proximal retainer disposed in the light source interface wherein the optic fiber bundle proximal end is disposed in the proximal retainer.

5. The interment of claim 1 wherein the optic fiber bundle comprises a single optic fiber.

6. The instrument of claim 1 wherein the optic fiber bundle comprises a plurality of optic fibers.

7. The instrument of claim 6 wherein the optic fiber bundle comprises at least two optic fibers and less than twenty optic fibers.

8. The instrument of claim 1 further comprising:
an aspiration tube having an aspiration tube distal end and an aspiration tube proximal end, the aspiration tube configured to facilitate an aspiration of a surgical site; and
a swivel having a swivel distal end and a swivel proximal end, the swivel configured to prevent a torqueing of the aspiration tube.

9. The instrument of claim 8 further comprising:
an outer swivel component of the swivel having an outer swivel component distal end and an outer swivel component proximal end; and
an inner swivel component of the swivel having an inner swivel component distal end and an inner swivel component proximal end.

10. The instrument of claim 9 wherein the outer swivel component is configured to rotate relative to the inner swivel component.

11. The instrument of claim 9 wherein the inner swivel component is configured to rotate relative to the outer swivel component.

12. The instrument of claim 1 further comprising:
a distal retainer having a distal retainer distal end and a distal retainer proximal end, the distal retainer disposed in the diffuser inner bore wherein the optic fiber bundle distal end is disposed in the distal retainer.

13. The instrument of claim 12 wherein the aspiration conduit is disposed in a medial bore of the distal retainer.

14. The instrument of claim 1 further comprising:
an atraumatic offset of the diffuser, the atraumatic offset configured to increase a surface area of a portion of the diffuser.

15. The instrument of claim 1 further comprising:
a diffusion notch of the diffuser, the diffusion notch configured to diffuse light by diffuse reflection.

16. The instrument of claim 1 further comprising:
a plurality of diffusion notches of the diffuser, each diffusion notch of the plurality of diffusion notches configured to diffuse light by diffuse reflection.

17. The instrument of claim 1 further comprising:
a diffusion indentation of the diffuser, the diffusion indentation configured to diffuse light by diffuse reflection.

18. The instrument of claim 1 further comprising:
a diffusion taper of the diffuser, the diffusion taper configured to diffuse light by diffuse reflection.

19. An instrument comprising:
a handle having a handle distal end and a handle proximal end;
an inner bore of the handle, the inner bore extending from the handle distal end to the handle proximal end;
a vent of the handle having a vent distal end and a vent proximal end, the vent configured to manipulate a pressure within the handle inner bore;
a diffuser having a diffuser distal end, a diffuser proximal end, and a diffuser inner bore;
an aspiration conduit having an aspiration conduit distal end and an aspiration conduit proximal end wherein the aspiration conduit distal end is disposed in the diffuser inner bore and the aspiration conduit proximal end is disposed in the inner bore of the handle;
an optic fiber bundle having an optic fiber bundle distal end and an optic fiber bundle proximal end, the optic fiber distal end disposed in the diffuser inner bore; and
is a distal retainer having a distal retainer distal end and a distal retainer proximal end, the distal retainer disposed the diffuser inner bore wherein the optic fiber bundle distal end is disposed in the distal retainer.

20. An instrument comprising:
a handle having a handle distal end and a handle proximal end;
an inner bore of the handle, the inner bore extending from the handle distal end to the handle proximal end;
a diffuser having a diffuser distal end, a diffuser proximal end, and a diffuser inner bore;
an aspiration conduit having an aspiration conduit distal end and an aspiration conduit proximal end wherein the aspiration conduit distal end is disposed in the diffuser inner bore and the aspiration conduit proximal end is disposed in the inner bore of the handle;
a light source interface having a light source interface distal end and a light source interface proximal end, the light source configured to interface with a surgical illumination machine;
an optic fiber bundle having an optic fiber bundle distal end and an optic fiber bundle proximal end, the optic fiber distal end disposed in the diffuser inner bore; and
a proximal retainer having a proximal retainer distal end and a proximal retainer proximal end, the proximal retainer disposed in the light source interface wherein the optic fiber bundle proximal end is disposed in the proximal retainer.

* * * * *